United States Patent [19]

Marshall et al.

[11] Patent Number: 5,420,032
[45] Date of Patent: May 30, 1995

[54] HOMING ENDONUCLEASE WHICH ORIGINATES FROM CHLAMYDOMONAS EUGAMETOS AND RECOGNIZES AND CLEAVES A 15, 17 OR 19 DEGENERATE DOUBLE STRANDED NUCLEOTIDE SEQUENCE

[75] Inventors: Philip Marshall, Chomedey Est; Claude Lemieux, Québec; Antonin Gauthier, Montréal; Monique Turmel, Québec, all of Canada

[73] Assignee: Universitge Laval, Quebec, Canada

[21] Appl. No.: 991,855

[22] Filed: Dec. 16, 1992

Related U.S. Application Data

[63] Continuation-in-part of Ser. No. 813,129, Dec. 23, 1991, abandoned.

[51] Int. Cl.$^6$ .................................................. C12N 9/22
[52] U.S. Cl. ......................................... 435/199; 435/257.6
[58] Field of Search ............................... 435/199, 257.6

[56] References Cited

PUBLICATIONS

Marshall et al., "Cleavage pattern of the homing endonuclease encoded by the fifth intron in the chloroplast large subunit rRNA-encoding gene of *Chlamydomonas eugametos*", *Gene*, 104:241–245 (1991).

B. Dujon et al., "Mobile Introns: Definition of Terms and Recommended Nomenclature", *Gene*, 82:115–118 (1989).

B. Lemieux et al., "Unidirectional gene conversions in the chloroplast of Chlamydomonas interspecific hybrids", *Mol. Gen. Genet.*, 212:48–55 (1980).

D. Bell-Pedersen et al., "I-*Tev*I, the Endonuclease Encoded by the Mobile td Intron, Recognizes Binding and Cleavage Domains on its DNA Target", *Proc. Natl. Acad. Sci. USA*, 88:7719–7723 (1991).

F. Chu, "Characterization of the Restriction Site of a Prokaryotic Intron-Encoded Endonuclease", *Proc. Natl. Acad. Sci. USA*, 87:3574–3578 (1990).

L. Colleaux et al., "Universal Code Equivalent of a Yeast Mitochondrial Intron Reading Frame is Expressed into E. coli as a Specific Double Strand Endonuclease", *Cell*, 44:521–523 (1986).

L. Colleaux et al., "Recognition and Cleavage Site of the Intron-Encoded *Omega* Transposase", *Proc. Natl. Acad. Sci. USA*, 85:6022–6026 (1988).

A. Delahodde et al., "Site-Specific DNA Endonculease and RNA Matruase Activities of Two Homologous Intron-Encoded Proteins from Yeast Mitochondria", *Cell*, 56:431–441 (1989).

A. Gauthier et al., "A Group I Intron in the Chloroplast Large Subunit rRNA Gene of *Chlamydomonas eugametos* Encodes a Double-Strand Endonuclease that Cleaves the Homing Site of this Intron", *Current Genetics*, 19:43–47 (1991).

C. Lemieux et al., "Nonreciprocal Recombination Between Alleles of the Chloroplast 23S rRNA Gene in Interspecific *Chlamydomonas* Crosses", *Proc. Natl. Acad. Sci. USA*, 84:4166–4170 (1987).

C. Moneihet et al., "Purification and Characterization of the in vitro activity of I-Sce I, a Novel and Highly Specific Endonuclease Encoded by a Group I Intron", *Nucleic Acid Research*, 18(6):1407–1413 (1990).

D. Muscarella et al., "A Mobile Group I Intron in the Nuclear rDNA of Physarum Polycephalum", *Cell*, 56:443–454 (1989).

(List continued on next page.)

*Primary Examiner*—Charles L. Patterson, Jr.
*Attorney, Agent, or Firm*—Merchant, Gould, Smith, Edell, Welter & Schmidt

[57] ABSTRACT

The present invention relates to a homing endonuclease which originates from *Chlamydomonas eugametos*, and was overproduced in *E. coli*, purified and characterized. The homing endonuclease of the present invention recognizes and cleaves degenerate double-stranded DNA at a specific recognition site; it particularly recognizes and cleaves 15, 17 and 19 nucleotide sequences. The cleavage of target DNA by this endonuclease produces a 4 nucleotide extension with a 3' OH overhang. A method to use the endonuclease of the present invention to cleave DNA fragments useful for gene mapping is also disclosed.

11 Claims, 7 Drawing Sheets

PUBLICATIONS

D. Muscarella et al., "Characterization of I-Ppo, an Intron-Encoded Endonuclease that Mediates Homing of a Group I Intron in the Ribosomal DNA of *Physarum polycephalum*", *Molecular and Cellular Biology*, 10(7):3386–3396 (1990).

F. Studier et al., "Use of Bacteriphage T7 RNA Polymerase to Direct Selective High-level Expression of Cloned Genes":, *J. Mol. Biol.*, 189:113–130 (1986).

J. M. Wenzlau et al., "A Latent Intron-Encoded Maturase Is Also an Endonuclease Needed for Intron Mobility", *Cell*, 56:421–430 (1989).

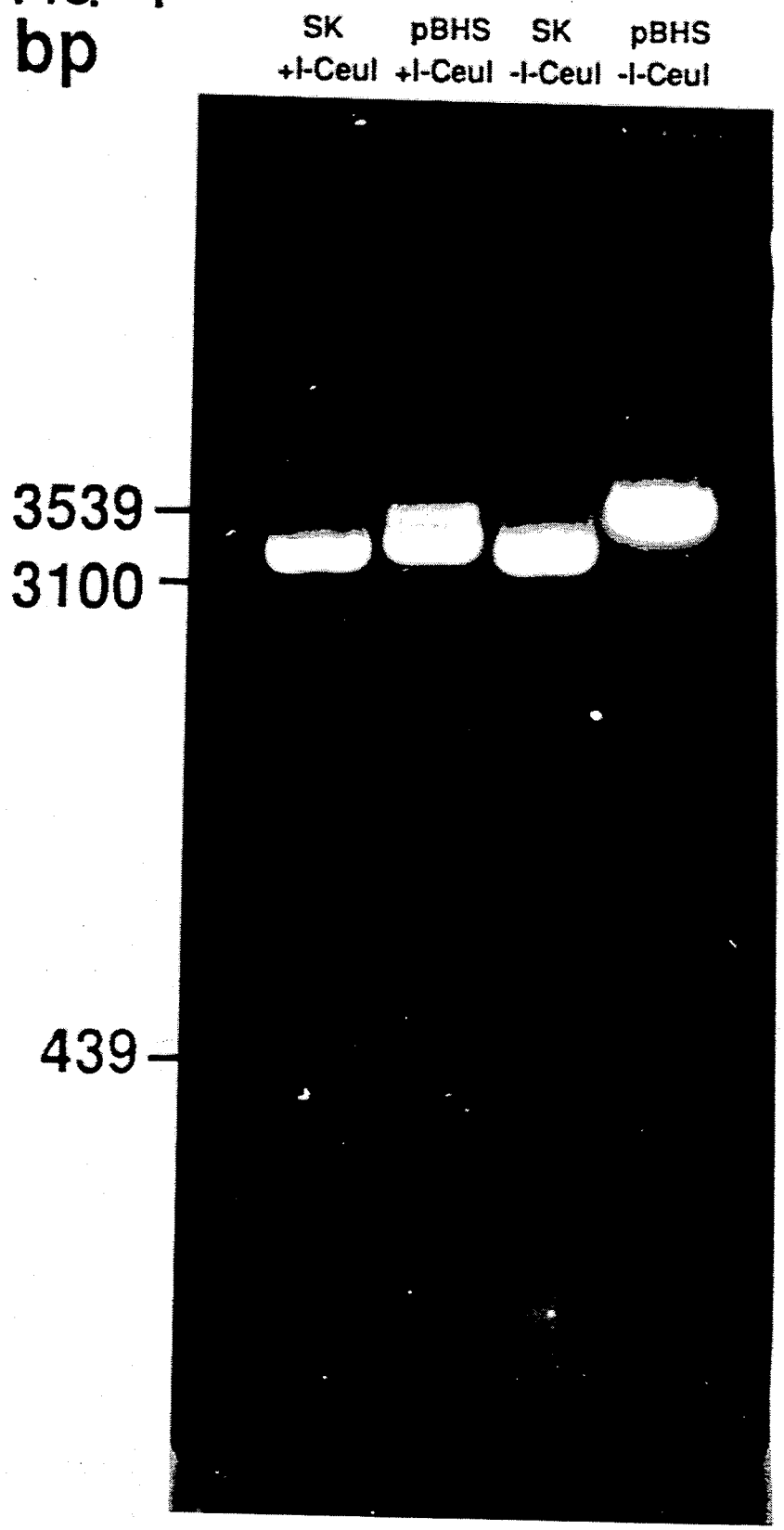

FIG. 9

I-Ceul
```
       ↓
CGGTCCTAA GGT
GCCAGGATTCCA
```

I-Ppol
```
         ↓
TCTCTTAA GGTA
AGAGAATTCCAT
```

I-SceI
```
       ↓
AGGGATAA CAGG
TCCCTATTGTCC
```

I-SceII
```
        ↓
GGTCACCCTGAA
CCAGTGGGACTT
```

I-TevI
```
               ↓
GTATCAAC GCTCAGTAGATGTTTCTTGGGTCTACC
CATAGTTGCGAGTCATCTACAAAGAACCCAGATGG
```

I-TevII
```
                        ↓
TGAGTATGAAGTGAACACGT TATTCA
ACTCATACTTCACTTGTGCAATAAGT
```

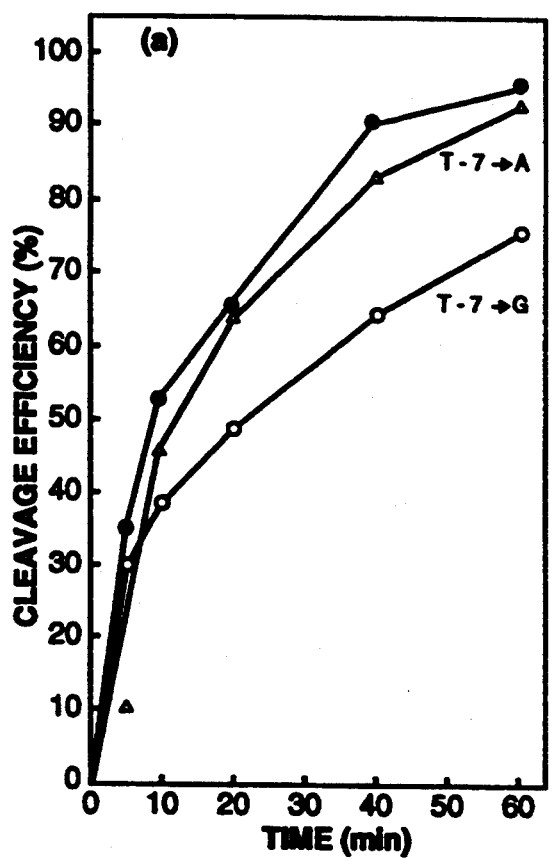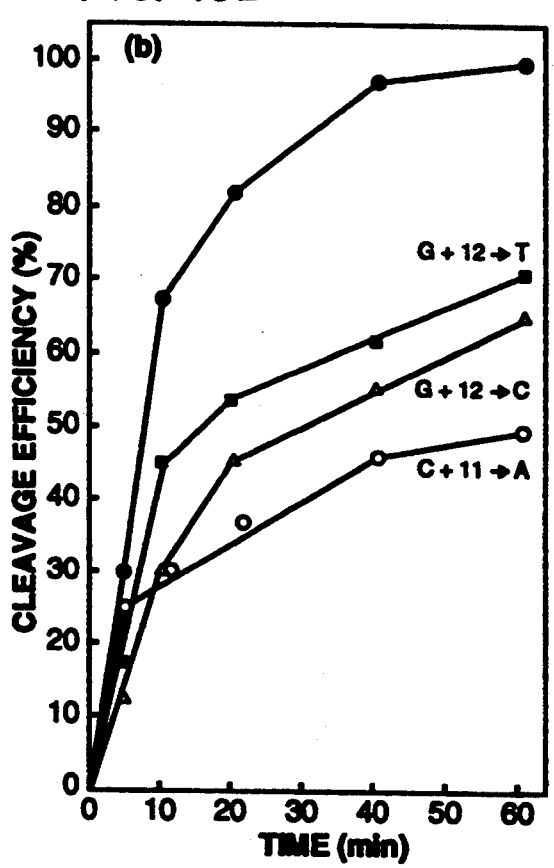

HOMING ENDONUCLEASE WHICH ORIGINATES FROM CHLAMYDOMONAS EUGAMETOS AND RECOGNIZES AND CLEAVES A 15, 17 OR 19 DEGENERATE DOUBLE STRANDED NUCLEOTIDE SEQUENCE

CROSS-REFERENCE TO RELATED APPLICATION

This application is a continuation-in-part of U.S. application Ser. No. 07/813,129, filed on Dec. 23, 1991, now abandoned.

BACKGROUND OF THE INVENTION

A few decades ago, genes were thought to exist as uninterrupted DNA units transcribed into corresponding mRNA sequences which are then translated by ribosomes to give proteins which serve a specific function in a cell.

One of the essential tools molecular biologists use to delve deeper into the mysteries of life contained in the structure of DNA, the genetic material, are molecular scissors called restriction endonuclease. There are many such enzymes which are capable of cutting DNA at specific sites.

Restriction enzymes (restriction endonucleases) recognize specific short sequences of DNA (usually unmethylated DNA) and cleave the duplex molecule, usually at the target recognition site, but sometimes elsewhere. In some instances, the recognition site is specific, but the cleavage site is located some distance away from the recognition site and does not appear to be at any specific sequence.

"Duplex" refers to the double stranded composition of the DNA molecule. The cleavage induced by endonucleases is usually at specific sequences of approximately 4 to 6 base pairs. A base pair is a union of purines of pyrimidines in the DNA duplex. There are four such bases and they pair in specific unions: adenine with thymine, (A-T), guanine with cytosine (G-C).

Restriction endonucleases are named by using three or four letter abbreviations identifying their origin, coupled with a letter and/or number designation which distinguish multiple enzymes of the same origin. An example of the nomenclature is EcoRI, one of the endonucleases derived from E. coli. Most of the endonucleases discovered initially were isolated from bacteria, in which they cleave DNA as part of the natural function of the cell. However, other organisms, for example, yeast, can be used as a source of double-strand DNA cleaving endonucleases.

Isolation of many endonucleases occurred because the bacteria from which the endonucleases were derived were able to distinguish between the DNA native to the bacteria and any invading foreign DNA. One of the ways bacteria recognize foreign DNA is by the absence of methyl groups at appropriate base pair sites. The bacteria protects its own DNA from cleavage by its own endonucleases, by methylation of its own DNA bases at appropriate target sites. Successful attack on bacteria by foreign DNA, for example by bacteriophages, may be due either to the fact that the phage DNA has the same methylation pattern as that of the host DNA, or alternatively, that mutations have caused defects in the ability of the bacteria to produce an endonuclease or to attack the foreign DNA. Endonucleases isolated from bacteria are of two types, one which is only able to cleave DNA, and another in which both restriction and methylation activities are combined. Some restriction endonucleases introduce staggered cuts with overhangs while others generate blunt ends.

Restriction endonucleases recognize unique sequences of generally 4 and 6 nucleotides in double-stranded DNA molecules and cleave only at or near these sites. Many of the known restriction enzymes recognize a palindromic sequence which bears a dyad (twofold) symmetry. Cleavage which occurs on both strands at the axis of symmetry will generate blunt-ended fragments. For example, the restriction endonuclease HpaI of the bacterium *Haemophilus parainfluenzae* recognizes a specific sequence and cleaves at the points designated by an arrow.

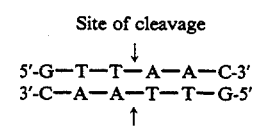

Site of cleavage

Thereby generating blunt-ended fragments.

Other restriction enzymes, such as Eco RI and Pst I will cleave both strands at similar positions on opposite sides of the axis and generate four nucleotide extensions that end respectively with a 5' phosphate and 3' hydroxyl group (Table 1).

TABLE 1

Specificity of some restriction endonucleases †

Producing flush ends

Hin dII    5'-G—T—Py—⁎Pu—A—C- 3'
           3'-C—A—Pu—Py—T—G- 5'

Hpa I      5'-G—T—T—A—A—C- 3'
           3'-C—A—A—T—T—G- 5'

Producing staggered ends

Eco RI     5'-G—A—A—T—T—C- 3'
           3'-C—T—T—A—A—G- 5'

Pst I      5'-C—T—G—C—A—G- 3'
           3'-G—A—C—G—T—C- 5'

Hin dIII   5'-A—A—G—C—T—T- 3'
           3'-T—T—C—G—A—A- 5'

† The dot indicates the axis of two-fold rotational symmetry, and the arrows indicate the site of cleavage. The asterisks show the methylation sites (where known) in the parent organism, which is *Haemophilus influenzae* for Hind II and Hind III, *E. coli* for Eco RI, *Providencia stuartii* for Pst I, and *Haemophilus parainfluenzae* for Hpa I. Pu = purine, Py = pyrimidine, and N = A or T.

Together with other recent developments, restriction endonucleases have made it possible to recombine genes from one organism into the genome of another. Another use of restriction endonucleases is to create and use cloning vectors for the transmission of DNA sequences. For this purpose, the gene of interest needs to be attached to the vector fragment. One way this may be accomplished is by generating complementary DNA sequences on the vector and on the gene of interest so that they can be united (recombined). Some restriction endonucleases make staggered cuts which generate short, complementary, single stranded "sticky ends" of the DNA. An example of such an action is that effected by the EcoRI endonuclease which cleaves each of the two strands of duplex DNA at a different point.

These cleavage sites lie on either side of a short sequence that is part of the site recognized by the endonuclease. When two different DNA molecules are cleaved with EcoRI the same sticky ends are generated which enables them to combine with each other. The DNA fragment can then be retrieved by cleaving the vector with EcoRI to release the gene.

Fragments generated by endonucleases are amenable for further analysis of their nucleotide composition. Variation in the fragment sizes obtained from the same chromosomal locations among individuals, is referred to as restriction fragment length polymorphism (RFLP).

Gene maps give the location of specific genes (specific DNA nucleotide sequences) that encode the primary sequences of protein gene products relative to each other and also localize the genes on specific chromosomes of higher organisms. A map of DNA obtained by using endonucleases to map breakpoints is called a restriction map and consists of a linear sequence of restriction sites. This physical map is obtained by extracting chromosomal DNA from the chromosomes in cells, breaking the extracted DNA at various points with endonucleases, and determining the order of restriction sites by analysis of the fragments.

Distances along the maps are measured directly in base pairs or, if distances are long, in megabase pairs. By comparing the sequences of DNA between relatively short distances, a DNA map is constructed in a stepwise fashion. A major goal of current research is to construct a map of the entire human genome. (The Human Genome Project, American Society of Human Genetics Symposium, Baltimore, Nov. 15, 1989.) Success in mapping human and animal genomes will require a selection of endonucleases which cleave at a large variety of sites which occur in the DNA of living organisms, not just in artificial sequences.

DNA fragments produced by the action of endonucleases are separated on the basis of size by agarose or polyacrylamide gel electrophoresis. An electric current is passed through the gel, causing the fragments to move down it at a rate depending on length; the smaller fragments move more rapidly. The result of this migration in a gel, is a series of bands each corresponding to a fragment of a particular size. Many different endonucleases are used for gene mapping, and large numbers of overlapping fragments are analyzed. Sequential cleavage using different endonucleases produces a series of larger fragments broken down into smaller fragments. A hierarchy is then constructed based on the fact that there is complete additivity of length of the fragments within the original starting fragment. For example, a fragment of 2,100 base pairs may be broken down into 200 and 1900 base pairs.

The establishment of restriction maps for genomes of several species revealed the existence of physically localized restriction fragment length polymorphisms (RFLP) that are used as physical markers to study recombination between genomes at the molecular level.

For the past years, studies that have focused on the inheritance of several genes have revealed that particular markers in these genes were inherited unidirectionally by the progeny from interspecific crosses. Comparative sequence analysis from both parents indicate that some of these markers are located within intervening sequences called introns that are usually found in either coding or non-coding sequences of a gene. These introns are then removed from the pre-mRNA transcripts by a process called "splicing". Sequences (exon) on each side of the intron are then brought together to form a mature m-RNA transcript. These introns belong to the group I family and contain internal open reading frames (ORF) which encode for endonucleases. These endonucleases generate a doublestrand cut at or near the site of intron insertion within the cognate allele and initiate a site-specific recombination event during which the intron is likely to be inserted by a gap repair mechanism. The net result is the elimination of intron-minus alleles and the propagation of intron-plus alleles into the progeny. This genetic phenomenon by which introns can be transmitted to the entire progeny is defined as an intron homing process.

The first homing intron that was discovered is the r1 intron in mitochondrial large subunit rRNA (LSU rRNA) gene of S. cerevisiae. This intron contains an ORF of 235 codons that codes for an endonuclease I-SceI which recognizes a non-symmetric sequence of 18 bp in the vicinity of the intron homing site and generates a 4 bp staggered cut with 3'OH overhangs.

Other homing endonucleases have been recently identified in the cox1 gene of S. cerevisiae mitochondria (I-SceII), in the nuclear LSU rRNA of P. polycephalum (I-PpoI) and in the td (I-TevI) and sun Y (I-TevII) genes of bacteriophage T4.

Although seemingly identical, in nature, to restriction endonucleases, homing endonucleases are different by their larger recognition sequence that extends up to 18 bp in comparison with 4 to 6 for restriction endonucleases. In opposition to restriction endonucleases which demonstrate a higher degree of sequence specificity, homing endonucleases exhibit recognition degeneracy towards their respective target sequence, that is, the cleavage efficiency at sites containing single-base mutations is the same as that at the wild-type site.

As essential components of methods used to construct restriction maps of smaller genomes, the use of restriction enzymes in mapping larger genomes is limited by their high frequency of cleavage.

Although recognition specificity of homing endonucleases appears to be less than that of restriction enzymes, their larger recognition sequence is susceptible to occur at a much lower frequency in large genomes.

Therefore, the homing endonucleases which generates larger DNA fragments will greatly facilitate the analysis (chromosomal mapping) of large genomes.

It would be highly desirable to provide a homing endonuclease which would recognize nucleotide sequences susceptible to occur at a much lesser frequency within a DNA sequence. Such an enzyme would generate larger DNA fragments which would facilitate, for instance, chromosomal mapping.

SUMMARY OF THE INVENTION

Surprisingly and in accordance with the present invention, there is provided a protein, more specifically a homing endonuclease encoded by the fifth intron of the LSU rRNA gene of the chloroplast genome of the unicellular green alga *Chlamydomonas eugametos*.

The homing endonuclease of the present invention is novel and extremely useful because it cleaves double-stranded DNA at specific, infrequent sites, for which endonucleases were not previously available. The resulting fragments are of great value for human gene mapping because the cleavage sites are sequences ordinarily encountered in genomic DNA, and because cleavage by the endonuclease produces relatively larger fragments than characteristic of those produced by many previously available endonucleases.

The homing endonuclease of the present invention is called I-CeuI and its recognition sequence was determined by random mutagenesis of nucleotide positions adjacent to the I-CeuI cleavage site. Single-base substitutions that completely abolish endonuclease activity delimit a 15-bp sequence whereas those that reduce the cleavage rate defined a 19-bp sequence that extends from position −7 to position +12 with respect to the CeLSU.5 intron insertion site. As the other homing endonucleases that have been studied so far, the I-CeuI endonuclease recognizes a non-symmetric degenerate sequence. The top strand of the recognition sequence is preferred for I-CeuI cleavage and the bottom strand most likely determines the rate of double-strand breaks.

More specifically, the endonuclease of the present invention recognizes and cleaves double-stranded DNA of the following 15, 17 or 19 bp sequences, bearing the following single-base substitutions which are illustrated as being underlined,

```
5'  ACG  GTC  CTA  AGG  TAG  3'   (SEQ ID NO:1)
3'  TGC  CAG  GAT  TCC  ATC  5'
5'  GCG  GTC  CTA  AGG  TAG  3'   (SEQ ID NO:2)
3'  CGC  CAG  GAT  TCC  ATC  5'
5'  ACT  GTC  CTA  AGG  TAG  3'   (SEQ ID NO:3)
3'  TGA  CAG  GAT  TCC  ATC  5'
5'  ACC  GTC  CTA  AGG  TAG  3'   (SEQ ID NO:4)
3'  TGG  CAG  GAT  TCC  ATC  5'
5'  ACG  GTC  CAA  AGG  TAG  3'   (SEQ ID NO:5)
3'  TGC  CAG  GTT  TCC  ATC  5'
5'  ACG  GTC  CTA  AGG  CAG  3'   (SEQ ID NO:6)
3'  TGC  CAG  GAT  TCC  GTC  5'
5'  ACG  GTC  CTA  AGG  TCG  3'   (SEQ ID NO:7)
3'  TGC  CAG  GAT  TCC  AGC  5'
5'  ACG  GTC  CTA  AGG  TTG  3'   (SEQ ID NO:8)
3'  TGC  CAG  GAT  TCC  AAC  5'
5'  TA  ACG  GTC  CTA  AGG  TAG  3'   (SEQ ID NO:9)
3'  AT  TGC  CAG  GAT  TCC  ATC  5'
5'  AA  ACG  GTC  CTA  AGG  TAG  3'   (SEQ ID NO:10)
3'  TT  TGC  CAG  GAT  TCC  ATC  5'
5'  GA  ACG  GTC  CTA  AGG  TAG  3'   (SEQ ID NO:11)
3'  CT  TGC  CAG  GAT  TCC  ATC  5'
5'  TT  ACG  GTC  CTA  AGG  TAG  3'   (SEQ ID NO:12)
3'  AA  TGC  CAG  GAT  TCC  ATC  3'
5'  TA  GCG  GTC  CTA  AGG  TAG  3'   (SEQ ID NO:13)
3'  AT  CGC  CAG  GAT  TCC  ATC  5'
5'  TA  ACT  GTC  CTA  AGG  TAG  3'   (SEQ ID NO:14)
3'  AT  TGA  CAG  GAT  TCC  ATC  5'
5'  TA  ACC  GTC  CTA  AGG  TAG  3'   (SEQ ID NO:15)
3'  AT  TCG  CAG  GAT  TCC  ATC  5'
5'  TA  ACG  GTC  CAA  AGG  TAG  3'   (SEQ ID NO:16)
3'  AT  TGC  CAG  GTT  TCC  ATC  5'
5'  TA  ACG  GTC  CTA  AGG  CAG  3'   (SEQ ID NO:17)
3'  AT  TGC  CAG  GAT  TCC  GTC  5'
5'  TA  ACG  GTC  CTA  AGG  TCG  3'   (SEQ ID NO:18)
3'  AT  TGC  CAG  GAT  TCC  AGC  5'
5'  TA  ACG  GTC  CTA  AGG  TTG  3'   (SEQ ID NO:19)
3'  AT  TGC  CAG  GAT  TCC  AAC  5'
5'  TA  ACG  GTC  CTA  AGG  TAG  CG  3'   (SEQ ID NO:20)
3'  AT  TGC  CAG  GAT  TCC  ATC  CG  5'
5'  AA  ACG  GTC  CTA  AGG  TAG  CG  3'   (SEQ ID NO:21)
3'  TT  TGC  CAG  GAT  TCC  ATC  GC  5'
5'  GA  ACG  GTC  CTA  AGG  TAG  CG  3'   (SEQ ID NO:22)
3'  CT  TGC  CAG  CAT  TCC  ATC  CG  5'
5'  TT  ACG  GTC  CTA  AGG  TAG  CG  3'   (SEQ ID NO:23)
3'  AA  TGC  CAG  GAT  TCC  ATC  CG  5'
5'  TA  GCG  GTC  CTA  AGG  TAG  CG  3'   (SEQ ID NO:24)
3'  AT  CGC  CAG  CAT  TCC  ATC  GC  5'
5'  TA  ACT  GTC  CTA  AGG  TAG  CG  3'   (SEQ ID NO:25)
3'  AT  TGA  CAG  CAT  TCC  ATC  GC  5'
5'  TA  ACC  GTC  CTA  AGG  TAG  CG  3'   (SEQ ID NO:26)
3'  AT  TCG  CAG  CAT  TCC  ATC  GC  5'
5'  TA  ACG  GTC  CAA  AGG  TAG  CG  3'   (SEQ ID NO:27)
3'  AT  TGC  CAG  GTT  TCC  ATC  GC  5'
5'  TA  ACG  GTC  CTA  AGG  CAG  CG  3'   (SEQ ID NO:28)
3'  AT  TGC  CAG  GAT  TCC  GTC  GC  5'
5'  TA  ACG  GTC  CTA  AGG  TCG  CG  3'   (SEQ ID NO:29)
3'  AT  TGC  CAG  GAT  TCC  AGC  GC  5'
5'  TA  ACG  GTC  CTA  AGG  TTG  CG  3'   (SEQ ID NO:30)
3'  AT  TGC  CAG  GAT  TCC  AAC  GC  5'
5'  TA  ACG  GTC  CTA  AGG  TAG  AG  3'   (SEQ ID NO:31)
3'  AT  TGC  CAG  GAT  TCC  ATC  TC  5'
5'  TA  ACG  GTC  CTA  AGG  TAG  CT  3'   (SEQ ID NO:32)
3'  AT  TGC  CAG  GAT  TCC  ATC  GA  5'
5'  TA  ACG  GTC  CTA  AGG  TAG  CC  3'   (SEQ ID NO:33)
```

| | | | | | | | |
|---|---|---|---|---|---|---|---|
| 3' AT | TGC | CAG | GAT | TCC | ATC | GG | 5' |

The I-CeuI endonuclease of the present invention generates from the 5' end of the upper strand a cut after the tenth nucleotide for the 15 nucleotide sequences or after the twelfth nucleotide for the 17 and 19 nucleotide sequences, and from the 5' end of the lower strand after the ninth nucleotide for the 15 and 17 nucleotide sequences or after the eleventh nucleotide for the 19 nucleotide sequences, thereby generating a 4 nucleotide extension with a 3'OH overhang.

Other advantages of the present invention will be readily illustrated by referring to the following description.

BRIEF DESCRIPTION OF THE DRAWINGS

FIG. 4 is the analysis, by agarose gel electrophoresis, of I-CeuI-BamHI cleavage products released from pBHS and pSK+Bluescript plasmid molecules.

FIG. 9 is the cleavage pattern of different homing endonucleases.

FIGS. 10A and 10B shows the effect of base-pair substitutions effected on the target DNA at position −7, +11 and +12 with respect of the intron insertion site, on the efficiency of cleavage by I-CeuI after a sixty-minute reaction.

DETAILED DESCRIPTION OF THE INVENTION

Physical evidence for recombination of chloroplast DNA was first noted in hybrid progeny recovered from crosses between the two interfertile species *Chlamydomonas eugametos* and *Chlamydomonas moewusii*. This evidence stemmed from the appearance in F1 hybrids of new restriction fragments that had not been previously observed in either *C. eugametos* or *C. moewusii* parents.

Although these results were useful in demonstrating the recombination events, they were useless in identifying the positions of these recombination events.

Subsequently, both the genomes of *C. eugametos* and *C. moewusii* were characterized by restriction mapping and then compared. This comparison revealed the existence of physically localized restriction length polymorphisms that can be used as physical markers to detect recombination events. For the past years, the inheritance of these polymorphic markers in *C. eugametos/C. moewusii* hybrids has been investigated. The first study has been focused on the inheritance of polymorphic markers of ribosomal genes within the inverted repeat of the chloroplast genome. This work revealed that an EcoRI restriction site unique to the *C. eugametos* chloroplast large subunit (LSU) rRNA gene is transmitted unidirectionally to the progeny, whatever the mating-type of the *C. eugametos* parent during interspecific crosses between *Chlamydomonas eugametos* and *Chlamydomonas moewusii*.

Comparative sequence analysis of the LSU rRNA gene from *C. eugametos* and *C. moewusii* indicates that this Eco RI is in the middle of an ORF of 218 amino acids that is located in an optional intron (CeLSU-5) that belongs to the group I family. This optional intron appears to be transmitted by duplicative transposition to an analogous position in the LSU gene of *C. moewusii* which is deficient for that intron.

Figure 1:
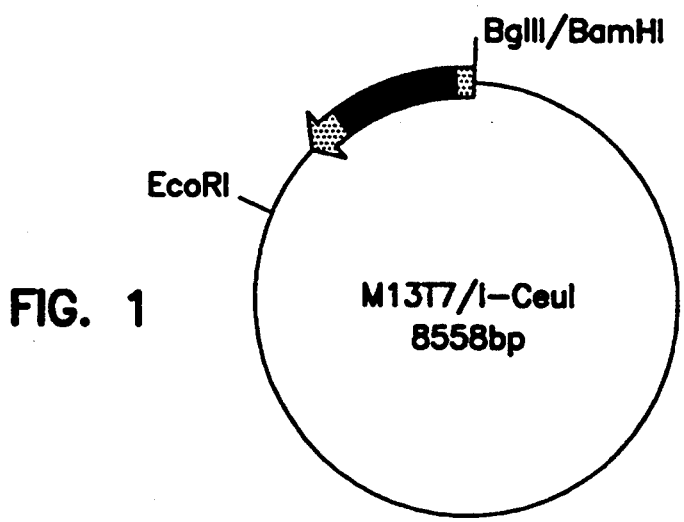
FIG. 1 is the physical map of the recombinant M13 bacteriophage (M13T7/I-Ceu-I).

Like the six other mobile introns that have been well characterized so far, CeLSU-5 contains a long open reading frame (ceuIR) coding for a site-specific endonuclease (I-CeuI) that cleaves the *C. moewusii* intronless gene in the vicinity of the intron-insertion site. This stimulates gap repair and mediates efficient transfer of the intron at its cognate site. By expressing the ceuIR gene in the *Escherichia coli* vectors pKK233-2 and pTRC-99A, it was recently demonstrated that the endonuclease is highly toxic to *E. coli*. To eliminate this problem and to characterize the cleavage pattern and the recognition sequence of the I-CeuI endonuclease, the ceuIR gene was expressed in *E. coli* under the control of a bacteriophage T7 promoter in a tightly regulated M13 (FIG. 1) system, and developed an in vitro system to assay partially purified I-CeuI activity.

It was then determined that the I-CeuI recognizes a sequence of 15 or 19 base pairs (bp) and produces a staggered cut by cutting, on one hand, after 5 bp downstream from the intron insertion site on the upper strand and by cutting after 1 bp downstream from the same site on the lower strand. The intron insertion site is represented below by an inverted triangle, and the staggered cut yields 4 nucleotide (CTAA or TTAG), 3'-OH overhangs.

The homing endonuclease of the present invention cleaves a target double-stranded DNA at said specific recognition site according to the following cutting pattern for a 15 bp sequence:

(SEQ ID NO: 1)

for a 17 bp sequence:

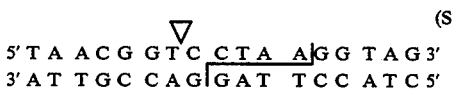

(SEQ ID NO: 9)

or for a 19 bp sequence:

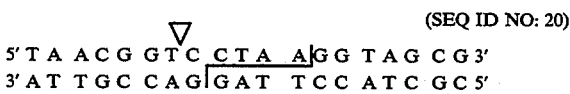

(SEQ ID NO: 20)

The present invention will be more readily understood by referring to the following examples which are given to illustrate the invention rather than to limit its scope.

EXAMPLE I

Expression of ceuIR gene in *Escherichia coli*

Partial purification of the endonuclease is made possible by the use of a strain or strains that overproduce the enzyme.

The ceuIR gene is expressed in M13 bacteriophage vectors. To this end, we cloned a fragment of the pET-8C plasmid that includes the promoter and terminator sequences of the T7 major capsid protein-encoding gene into the M13mp18 vector (FIG. 1), and inserted the ceuIR gene at the NcoI site located downstream from the T7 promoter.

To construct this recombinant bacteriophage, the approach employed by Gauthier et al. (CURRENT. GENETICS., 1991, 19, pp. 43–47) to introduce the ceuIR gene into the *E. coli* vectors pKK233-2 and pTRC-99A was essentially used. A 712-bp HpaII-TaqI fragment containing all but the first 22 bp of the ceuIR gene was ligated to an adaptor consisting of the annealed oligos 5'-CATGTCCAACTTCATCCTGAAAC (SEQ ID NO. 34) and

5'-CGGTTTCAGGATGAAGTTGGA (SEQ ID NO. 35)

(only the latter was phosphorylated). The resulting 750-bp fragment (FIG. 2 blackened box) was isolated by electrophoresis in a low-melting-temperature agarose gel, phosphorylated and cloned into the NcoI site of the M13T7 expression vector. This vector was constructed by isolating the 650-bp BglII-EcoRI fragment (FIG. 2 hatched boxes) from the pET-8C plasmid, which contains the promoter and terminator sequences of the T7 major capsid protein-encoding gene, and inserting this fragment between the BamHI and EcoRI sites of M13mp18. Ligation mixtures were used to transfect *E. coli* DH5αFIQ cells (BRL) as described by manufacturer and the recombinant M13T7/I-CeuI bacteriophages with the correct orientation and phase of the ceuIR gene were identified by restriction and sequence analyses.

The resulting construct, called M13T7/I-CeuI (FIG. 1), proved to be stable in *E. coli*, suggesting that the expression of the toxic endonuclease is maintained to a low level in this system. The increased stability of the ceuIR gene in M13 may be explained by a tighter regulation of gene expression as compared to plasmid expression vectors.

Figure 2:
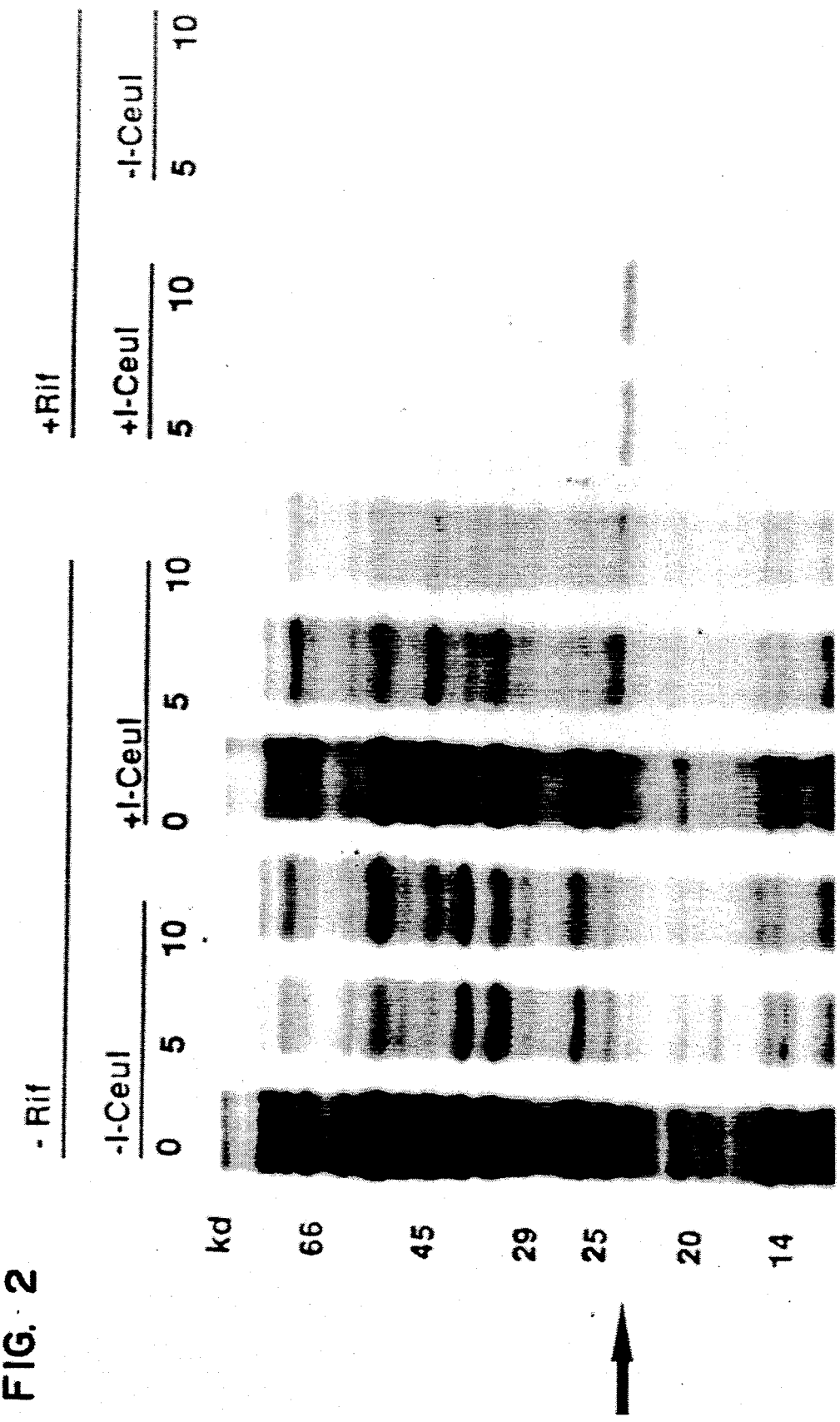
FIG. 2 is the analysis on denaturing SDS-polyacrylamide gel of pulse-labelled proteins from an I-CeuI overproducing strain.

A polypeptide with the expected size of the ceuIR gene product (about 25 kDa) is produced when *E. coli* JM101, carrying the M13T7/I-CeuI construct, are infected with the λCE6 bacteriophage (FIG. 2).

Pulse-labelling of protein was performed as described by Studier and Moffat (J. MOL. BIOL., F. W. Studier & B. Moffat, 1986, 189, pp. 113–130) with the following modifications. A 10-ml culture of *E. coli* JM101 was grown in M9 minimal medium with 0.2% maltose under vigorous agitation (220 rpm) to an $A_{550nm}$ of 0.3 and the cells were infected with an excess of recombinant M13T7/I-CeuI (+I-CeuI) or M13T7 (−I-CeuI) bacteriophages (10 pfu/cell). When the cultures reached an $A_{550nm}$ of 0.6, aliquots of 1 ml were infected with λCE6 bacteriophage at moi of 0,5 and 10, incubated for a period of 60 min. under the same culture conditions, and pulse-labelled for 10 min. with 12.5 µCi of 2-3-4-5[$^3$H]leucine (ICN, 110 Ci/mmol) in the absence (−Rif) or presence (+Rif) of rifampicin at a final concentration of 200 µg/ml. After labelling, the cells were centrifuged and resuspended in sample buffer (80 mM Tris-HCl pH 6.8/0.1M DTT/2%) sodium dodecyl sulfate/10% glycerol/0.0012% bromophenol blue). The protein samples were boiled for 3 min. and analyzed on denaturing 15% polyacrylamide gels. Note that a polypeptide of about 25 kDa (arrow) is detected only in cells containing the M13T7/I-CeuI construct.

This polypeptide is detected only in cells containing the M13T7/I-CeuI construct and its production is maintained in pulse-labelling experiments carried out in the presence of rifampicin, and antibiotic that inhibits the RNA polymerase of *E. coli* but not that of bacteriophage T7. This suggests that the about 25-kDa polypeptide is the product of the ceuIR gene. Its presence can be easily visualized on polyacrylamide gels stained with Coomassie blue, indicating that the yield represents a significant proportion of the *E. coli* proteins.

Figure 3:
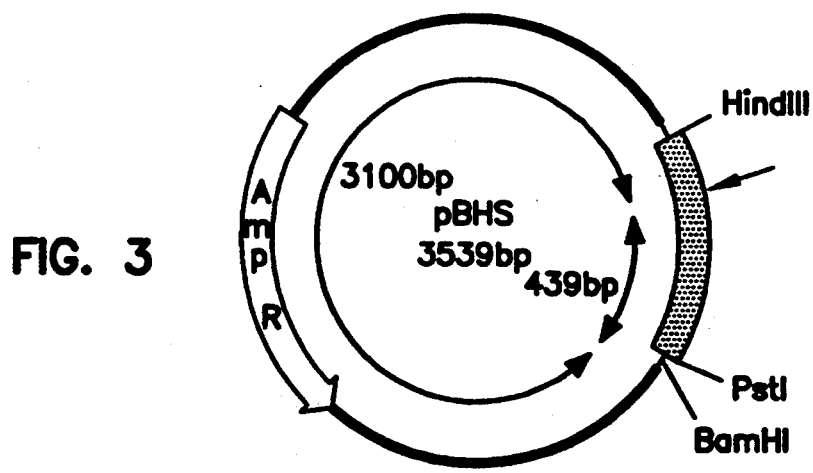
FIG. 3 is a physical map of plasmid pBHS.

To confirm the nature of the about 25-kDa polypeptide, partially purified extracts of infected *E. coli* cells carrying the M13T7/I-CeuI construct were assayed in vitro for ENase activity. Following incubation of *E. coli* extracts with a plasmid that contains the CeLSU-5 homing site as a source of I-CeuI cleavage site (pBHS, FIG. 3) and restriction of the reaction products with an enzyme that cleaves at a single site within pBHS (BamHI), active I-CeuI fractions revealed fragments of 3100 and 439 bp in agarose gels while inactive or control extracts revealed only the linearized pBHS plasmid (FIG. 4). Plasmid pBHS was constructed by introducing a 575-bp HindIII-PstI fragment from *C. moewusii* in the pBluescript SK-vector (Stratagene, La Jolla, Calif.) cleaved by the same restriction enzymes. This fragment contains the insertion site of the CeLSU-5 intron (arrow) and encompasses the last 275 bp of the fourth intron and the first 300 bp of the fifth exon of the LSU rRNA-encoding gene of *C. moewusii*. Sizes and positions of fragments generated by cleavage with I-CeuI and BamHI are indicated by the circular arrows.

EXAMPLE II

Assays for endonuclease activity

For an in vitro assay of endonuclease activity, the restriction site of 15, 17 or 19 bp DNA sequence, plus flanking DNA sequences is introduced into various plasmids. Essentially, any plasmid DNA containing the cut site is suitable. For the assays described herein, the plasmid pBHS containing a 575 bp Pst I-Hind III fragment that includes the I-CeuI recognition site from *C. moewusii* cloned into the vector SK+Bluescript from Stratagene (La Jolla, Calif.) is used.

Active I-CeuI preparations (+) and control extracts (−) were assayed in vitro for ENase activity on the plasmids pBHS and pBluescipt SK+ (SK) by incubation with 0.5 µg of Cs-Cl-purified plasmid DNA in the following conditions: 25 mM Tris-HCl pH 7.5/50 mM NaCl/10 mM MgCl$_2$/1 mM DTT, at 37° C. for 60 min. (FIG. 4). The reaction products were then phenol-extracted, ethanol-precipitated, digested with BamHI and submitted to agarose-gel electrophoresis. Active I-CeuI fractions are revealed by the presence of the 3100- and 439-bp fragments. *E. coli* extracts with I-CeuI activity were prepared and purified as follows. A 500-ml culture of *E. coli* JM101 containing the M13T7/I-

CeuI recombinant bacteriophage was infected with λCE6 bacteriophage at a moi of 5. One hour after the infection, cells were harvested, resuspended in 10 ml of buffer A (50 mM Tris-HCl pH 7.5/100 mM NaCl/2 mR EDTA/2 mM DTT/10% glycerol) containing 0.1 mM phenylmethylsulfonyl fluoride and 1 mg lysozyme per ml, and sonicated for 1 min. After centrifugation at 20,000×g for 20 min. at 4° C., the supernatant was passed through a 50-ml column of CELLEX-D (BioRad) equilibrated with buffer A at 4° C. The column was eluted with the same buffer at a flow rate of 2 ml/min., and a 50 μl aliquot of each fraction was tested for I-CeuI activity as described above.

Although we have observed complete digestion of the I-CeuI cleavage site with several independent ENase preparations, it is obvious that attempts to optimize the conditions for in vitro cleavage will require further purification of the endonuclease activity as contaminants present in the extracts are likely to affect these conditions.

EXAMPLE III

I-CeuI endonuclease acts upon the locus of intron insertion

Although the cleavage sites of homing ENases have not always been mapped in close proximity of the intron insertion sites (FIG. 9), it is currently believed that the recognition sequences of these endonucleases are centered around the insertion site.

Figure 5:
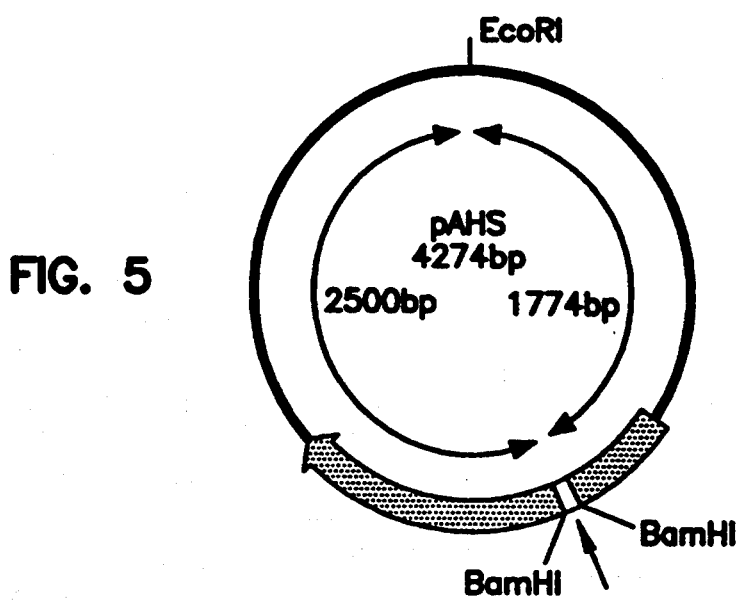
FIG. 5 is a physical map of pAHS plasmid.
Figure 6:
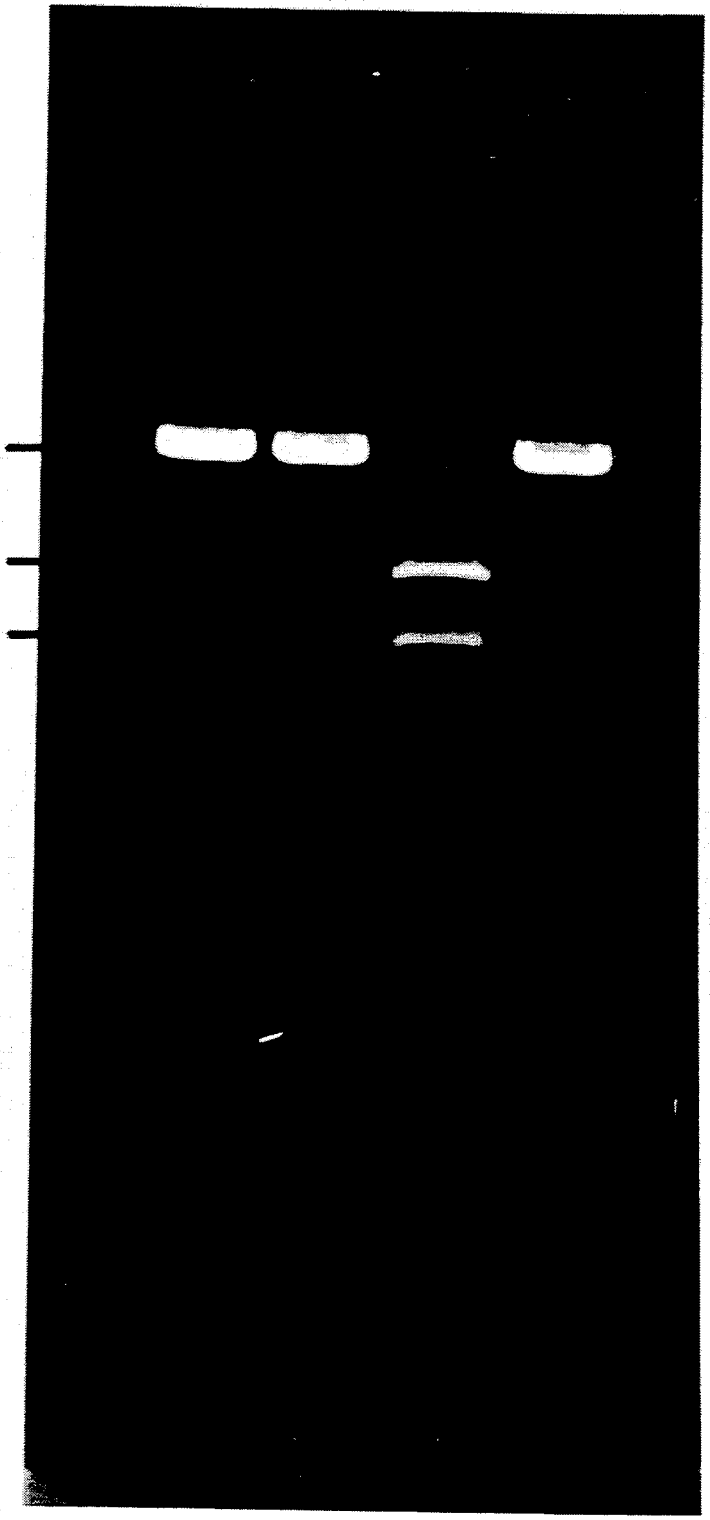
FIG. 6 is the analysis, by agarose gel electrophoresis, of I-CeuI-EcoRI cleavage products released from pAHS and pACYC184 plasmid molecules.

In an attempt to map the recognition sequence of I-CeuI, we cloned a synthetic 26-bp DNA fragment encompassing the CeLSU-5 insertion site in pACYC184 and tested whether the recombinant plasmid (pAHS) (FIG. 5), was cleaved by our partially purified endonuclease preparation. Plasmid pAHS proved to be easily cleaved by these preparations (FIG. 6), indicating the I-CeuI recognition and cleavage are directed by a short nucleotide sequence of less that 26 bp in the immediate vicinity of the intron insertion site.

To construct the pAHS plasmid, a synthetic 26-bp DNA fragment encompassing the CeLSU-5 homing site (arrow) was cloned into the BamHI site of the pACYC184 vector. The 26-bp fragment consists of the annealed oligos 5'-GATCCTAACTATAACGGTCCTAAGG-
TAGCGAG (SEQ ID NO. 36) and

5'GATCCTCGCTACCTTAGGACCGT-
TATAGTTAG (SEQ ID NO. 37).

Size and positions of the fragments generated by cleavage with I-CeuI and EcoRI are indicated by the "circular" arrows. The shaded box represents the gene encoding resistance to tetracycline. Active I-CeuI preparations (+) and control extracts (−) were assayed in vitro for endonuclease activity on pAHS and pACYC184 (pACYC). Following digestion of the reaction products with EcoRI, cleavage of the I-CeuI site revealed by the presence of the 2500 and 1774 bp fragments.

EXAMPLE IV

Cleavage pattern

Figure 7:
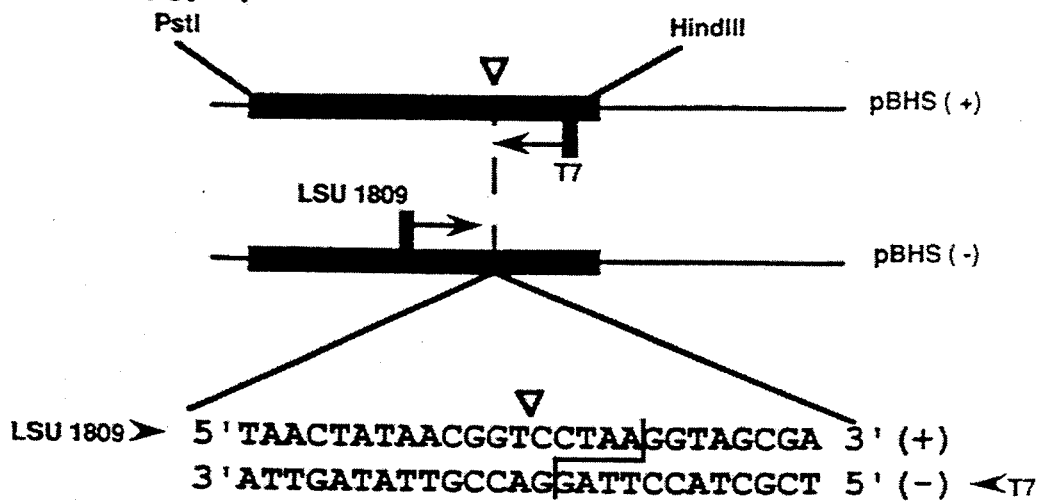
FIG. 7 is the strategy used to map the I-CeuI cleavage site.
Figure 8:
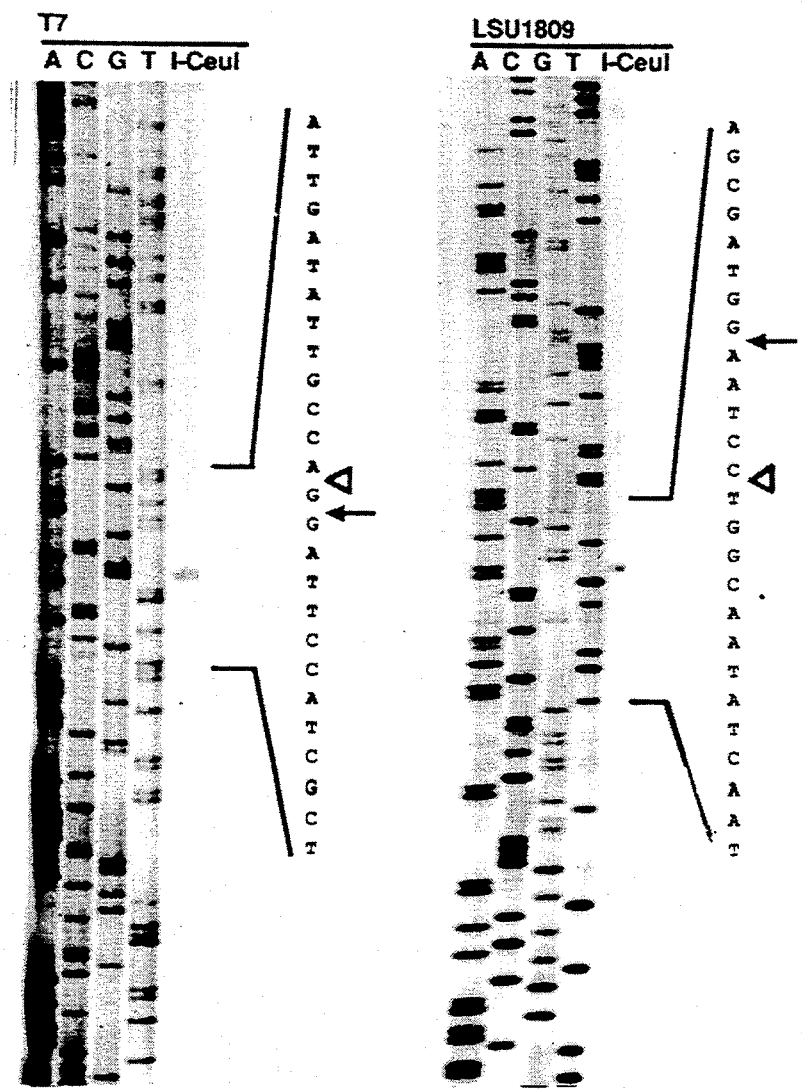
FIG. 8 is the analysis on 4% polyacrylamide-8M urea gels of sequencing reactions encompassing the I-CeuI cleavage site, alongside with 5' labelled I-CeuI cleavage products.

The nature of the I-CeuI cleavage site was determined essentially as described by Wenzlau et al. (CELL, J. M. Wenzlau et al., 1989, 56, pp. 421-430). We found that cleavage of a 575-bp *C. moewusii* sequence encompassing the CeLSU-5 insertion site occurs 5 bp downstream from this site and generates a 4 nucleotide (CTAA) extension with 3'-OH overhangs (FIGS. 7 and 8).

The I-CeuI cleavage site was defined as described by Wenzlau et al. (1989), using oligo primers that map 110 bp downstream (T7) and 140 bp upstream (LSU1809) from the CeLSU-5 insertion site (open triangle). Single-stranded pBHS (−) DNA corresponding to the RNA-like strand of the *C. moewusii* chloroplast LSU rRNA-encoding gene was annealed to 5 ng of $^{32}$p-labelled LSU1809 oligo primer (5'-ACAGGTCTCC-GCAAAGTCGTA; SEQ ID NO. 38) while pBHS (+) DNA corresponding to the opposite DNA strand was annealed to 5 ng of the $^{32}$p-labelled T7 oligo primer (5'-AATACGACTCACTATAG; SEQ ID NO. 39). The annealed mixtures were elongated for (arrowheads) with PolIk in the presence of 2 mM deoxyribonucleotide triphosphate/50 mM Tris-HCl pH 7.5/50 mM NaCl/10 mM MgCl$_2$ at 25° C. for 30 min. and cleaved with a preparation of I-CeuI under the conditions described for FIG. 3. The cleavage pattern of the endonuclease is represented by the staggered line on the nucleotide sequence. The cleavage products were phenol-extracted, ethanol-precipitated, resuspended in sequencing loading buffer and resolved in sequencing 4% polyacrylamide urea gels alongside M13 sequencing reactions of the corresponding DNA templates (FIG. 8). Lanes are labelled with the complementary dideoxynucleotides utilized in the sequencing reactions and arrowheads indicate the positions corresponding to the 3' termini of the cleavage products (I-CeuI lane).

It is interesting to note that cleavage, denoted by solid lines in FIG. 9, by the I-CeuI and I-PpoI endonucleases occurs at same relative positions within the *C. moewusii* chloroplast and the *P. polycephalum* nuclear LSU rRNA-encoding genes, i.e., at a position corresponding to nt 1928-1929 in the *E. coli* 23S/rRNA. The cleavage pattern of I-CeuI (FIG. 9) is very similar to those produced by the mitochondrial I-SceI and I-SceII and the nuclear I-PpoI endonucleases, and is significantly different from those generated by the bacteriophage I-TevI and I-TevII endonucleases. This observation supports the current idea that homing endonucleases originating from eukaryotic compartments cleave at close proximity of the intron insertion site, whereas bacteriophage endonucleases cleave at a distance from these sites. It should be emphasized, however, that these differences in cleavage pattern are relatively subtle when one considers the relative position of homing sites. According to the ds break repair model, exonuclease degradation proceeding from the gap site and leaving two molecules with long single-stranded 3'-OH tails is expected to occur after cleavage by homing endonuclease. As the intron insertion sites that have been mapped most distantly from the endonuclease cleavage sites are likely to be included in these single-stranded DNA tails, one could speculate that the subtle differences observed between the cleavage pattern of eukaryotic and bacteriophage endonucleases have little or no consequences on the molecular mechanisms underlying the intron homing process. The finding of mobile introns reinforces the idea that introns originated as parasites that invaded host genomes during evolution. Because the insertion site of the CeLSU-5 intron in the chloroplast LSU rRNA-encoding gene of Chlamydomonas map very closely to those of intron 3 in the nuclear LSU rRNA-encoding gene of *P. polycephalum* and the unique intron in the nuclear LSU rRNA-encoding gene of *Tetrahymena thermophila*, one might suggest the existence of hotspots for intron insertion sites. It is still unclear, however, if the endonuclease encoding genes that confer intron mobility were involved in the spread of introns from one genomic site to another. Even though many questions remain to be answered, the characterization of mobile introns and their homing endonucleases may help to elucidate the chain of events that lead to the proliferation of group-I introns in certain organelle genomes, such as the Podospora mitochondrial and Chlamydomonas chloroplast DNAs.

EXAMPLE V

Recognition sequence of the I-CeuI homing endonuclease

The recognition sequence of this I-CeuI homing endonuclease was determined by introducing 39 single-base substitutions in a short oligonucleotide of 26 bp centered away from the intron insertion site. These mutants were cloned in a SK+ bluescript vector and verified by sequence analysis. Fragments generated by a double-strand cut at these sites were separated by electrophoresis and stained with ethidium bromide (a dye that intercalates at every 4 bases in the DNA and fluoresces when exposed to U.V. light). The cleavage efficiency at these mutant sites was determined by comparing the relative fluorescence intensity of fragments generated with the intensity of fragments generated by cleavage at the wild type site. Changes in the oligonucleotide which diminish cleavage efficiency by not more than 60% delimit a recognition sequence of 19 bp whereas mutations that almost abolish completely endonuclease activity reduce the length of the recognition sequence to 15 bp. This is exemplified by the results shown in Table 2 and FIG. 10. After a long period of incubation, the target DNA bearing base-pair substitutions at positions $-5$ or $+10$ are almost not cleaved by I-CeuI (values lower than 20%). These positions therefore delimit the minimal sequence recognized and cleaved by this endonuclease. When base-pair substitutions are effected at positions $-7$, $+11$ or $+12$, the so mutated target DNAs are very efficiently cleaved after a long period of incubation, as shown in Table 2, while a short period of incubation of sixty minutes, as shown in FIG. 10, demonstrates that the so mutated target DNAs are cleaved with an efficiency which can be as low as 45% of the efficiency of cleavage of the wild-type target DNA. These positions therefore delimit a 19 base-pair sequence within which base-pair substitutions can occur and only reduce (but not abolish) the efficiency of cleavage by I-CeuI.

TABLE 2

Mutation within a 28 nucleotide sequence recognized by the I-CeuI endonuclease

|  | −13 | −12 | −11 | −10 | −9 | −8 | −7 | −6 | −5 | −4 | −3 | −2 | −1 | 1 | 2 | 3 | 4 | 5 | 6 | 7 | 8 | 9 | 10 | 11 | 12 | 13 |
|---|---|---|---|---|---|---|---|---|---|---|---|---|---|---|---|---|---|---|---|---|---|---|---|---|---|---|
| C | T | A | A | C | T | A | T | A | A | C | G | G | T | C | C | T | A | A | G | G | T | A | G | C | G | A |
| G | A | T | T | G | A | T | A | T | T | G | C | C | A | G | G | A | T | T | C | C | A | T | C | G | C | T |
|  |  | ← | | | | 19 bp | | | | | | | | | | | | | | | | → | | | | |
|  |  |  |  |  |  |  |  |  |  | ← | | | | | 15 bp | | | | | | → | | | | |  |
|  |  | D2 100 |  |  | 96 | 98 | 454 98; 84 | 99 | C14 96; 0 | 14 | 0 | 15 | F3 0 | 0 | 63 | | 10 | 0 | 13 | 0 | | 76 | 88 | 87 | | 100 | |
|  |  |  |  |  |  |  | 453 |  |  |  |  |  |  | 2JB 0 | 1 JA |  |  |  | SJC 84 5; 8 |  |  |  | C3 19C 0 | 2J2 89 |  |  |
|  |  | A14 |  |  | 25 | 7 100 |  | F23 | E17 0 | F2 0 | 17 JC 100; 70 | 11 B62 0 | 20 |  |  | 21 |  | 14 JB 0 |  | B13 | 3JC 73 |  |  |  |  |  |
|  |  |  |  |  |  | 16 J2 |  |  | 7C |  |  |  |  |  |  | D6 | 2J4 |  |  | E16 | E19 | 32 JA | | E3 | | A9 |
| 19 JC | A12 | E9 | 100 | 100 |  |  |  |  |  |  |  |  |  |  |  |  |  |  |  |  |  | E19 97 |  |  |  |  |  |

The numbers at the top rows of the grid correspond to the nucleotide sequence of a short oligonucleotide in which single-base mutations were induced at positions numbered from −13 to +14. All possible substitutions are represented by letters on the extreme left. Mutants tested are designated at the bottom of spaces and the cleavage efficiency allowed by these mutations is expressed as a percentage at the top. For in vitro endonuclease assays, 300 ng of recombinant substrate, bearing either wild-type or mutant sites, were incubated at 37° C. for 16 hours in the presence of one (1) arbitrary unit (1 unit is the amount of I-CeuI required for complete cleavage of 1 μg of pBHS). The maximum boundaries of the I-CeuI recognition sequence are defined by bilateral arrows above the grid.

Therefore, the following sequences are recognized by the I-CeuI endonuclease of the present invention:

```
5' ACG GTC CTA AGG TAG       3'  (SEQ ID NO:1)
3' TGC CAG GAT TCC ATC       5'
5' GCG GTC CTA AGG TAG       3'  (SEQ ID NO:2)
3' CGC CAG GAT TCC ATC       5'
5' ACT GTC CTA AGG TAG       3'  (SEQ ID NO:3)
3' TGA CAG GAT TCC ATC       5'
5' ACC GTC CTA AGG TAG       3'  (SEQ ID NO:4)
3' TGG CAG GAT TCC ATC       5'
5' ACG GTC CAA AGG TAG       3'  (SEQ ID NO:5)
3' TGC CAG GTT TCC ATC       5'
5' ACG GTC CTA AGG CAG       3'  (SEQ ID NO:6)
3' TGC CAG GAT TCC GTC       5'
5' ACG GTC CTA AGG TCG       3'  (SEQ ID NO:7)
3' TGC CAG GAT TCC AGC       5'
5' ACG GTC CTA AGG TTG       3'  (SEQ ID NO:8)
3' TGC CAG GAT TCC AAC       5'
5' TA ACG GTC CTA AGG TAG    3'  (SEQ ID NO:9)
3' AT TGC CAG GAT TCC ATC    5'
5' AA ACG GTC CTA AGG TAG    3'  (SEQ ID NO:10)
3' TT TGC CAG GAT TCC ATC    5'
5' GA ACG GTC CTA AGG TAG    3'  (SEQ ID NO:11)
3' CT TGC CAG GAT TCC ATC    5'
5' TT ACG GTC CTA AGG TAG    3'  (SEQ ID NO:12)
3' AA TGC CAG GAT TCC ATC    3'
5' TA GCG GTC CTA AGG TAG    3'  (SEQ ID NO:13)
3' AT CGC CAG GAT TCC ATC    5'
5' TA ACT GTC CTA AGG TAG    3'  (SEQ ID NO:14)
3' AT TGA CAG GAT TCC ATC    5'
5' TA ACC GTC CTA AGG TAG    3'  (SEQ ID NO:15)
3' AT TCG CAG GAT TCC ATC    5'
5' TA ACG GTC CAA AGG TAG    3'  (SEQ ID NO:16)
3' AT TGC CAG GTT TCC ATC    5'
5' TA ACG GTC CTA AGG CAG    3'  (SEQ ID NO:17)
3' AT TGC CAG GAT TCC GTC    5'
5' TA ACG GTC CTA AGG TCG    3'  (SEQ ID NO:18)
3' AT TGC CAG GAT TCC AGC    5'
5' TA ACG GTC CTA AGG TTG    3'  (SEQ ID NO:19)
3' AT TGC CAG GAT TCC AAC    5'
5' TA ACG GTC CTA AGG TAG CG 3'  (SEQ ID NO:20)
3' AT TGC CAG GAT TCC ATC CG 5'
5' AA ACG GTC CTA AGG TAG CG 3'  (SEQ ID NO:21)
3' TT TGC CAG GAT TCC ATC GC 5'
5' GA ACG GTC CTA AGG TAG CG 3'  (SEQ ID NO:22)
3' CT TGC CAG CAT TCC ATC CG 5'
5' TT ACG GTC CTA AGG TAG CG 3'  (SEQ ID NO:23)
3' AA TGC CAG GAT TCC ATC CG 5'
5' TA GCG GTC CTA AGG TAG CG 3'  (SEQ ID NO:24)
3' AT CGC CAG CAT TCC ATC GC 5'
5' TA ACT GTC CTA AGG TAG CG 3'  (SEQ ID NO:25)
3' AT TGA CAG CAT TCC ATC GC 5'
5' TA ACC GTC CTA AGG TAG CG 3'  (SEQ ID NO:26)
3' AT TCG CAG CAT TCC ATC GC 5'
5' TA ACG GTC CAA AGG TAG CG 3'  (SEQ ID NO:27)
3' AT TGC CAG GTT TCC ATC GC 5'
5' TA ACG GTC CTA AGG CAG CG 3'  (SEQ ID NO:28)
3' AT TGC CAG GAT TCC GTC GC 5'
5' TA ACG GTC CTA AGG TCG CG 3'  (SEQ ID NO:29)
3' AT TGC CAG GAT TCC AGC GC 5'
5' TA ACG GTC CTA AGG TTG CG 3'  (SEQ ID NO:30)
3' AT TGC CAG GAT TCC AAC GC 5'
5' TA ACG GTC CTA AGG TAG AG 3'  (SEQ ID NO:31)
3' AT TGC CAG GAT TCC ATC TC 5'
5' TA ACG GTC CTA AGG TAG CT 3'  (SEQ ID NO:32)
3' AT TGC CAG GAT TCC ATC GA 5'
5' TA ACG GTC CTA AGG TAG CC 3'  (SEQ ID NO:33)
3' AT TGC CAG GAT TCC ATC GG 5'
```

All of the above results demonstrate that naturally occurring or synthetic substrates bearing base-pair substitutions (degenerate DNA sequence) can be recognized and cleaved by I-CeuI, a novel homing endonuclease, which will be useful as a "restriction" enzyme for cleaving low frequency sequence, because of its long recognition sequence.

Even if all substitution combinations have not been obtained, including multiple substitutions, the above results, that is, demonstrating the recognition of degenerate sequence by I-CeuI, can be reasonably extended to substrates bearing such non-experimented substitutions, single, or multiple.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated endonuclease from *Chlamydomonas eugametos* which recognizes and cuts at a recognition sequence in a degenerate double-stranded target DNA sequence, wherein said recognition sequence includes the following nucleic acid sequence:

```
5' CCN   AA| GG 3'
3' G| GN' TTC  C 5'
``` and wherein N is T or A and N' is T or A and wherein the staggered line represents where the endonuclease cuts the degenerate double-stranded target DNA sequence.

2. An isolated endonuclease originating from the chloroplast of unicellular green algae *Chlamydomonas eugametos* which recognizes and cleaves a degenerate double-stranded target DNA sequence, said endonuclease, when encountered in its natural environment, is involved in an intron homing process, said process being defined by the insertion of an intron in an insertion site of a corresponding allele, said insertion involving recognition and cleavage of both strands of a naturally occurring wild-type sequence consisting essentially of at least a part of the following nucleic acid sequence by said endonuclease:

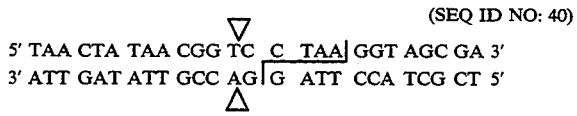

(SEQ ID NO: 40)

wherein said insertion site is represented by the open triangles and the cleavage on both strands is represented by a staggered line; said cleavage being effected by cutting after the fifth nucleotide downstream from said insertion site on the upper strand of said wild-type sequence, and by cutting before the first nucleotide upstream from said insertion site on the lower stand of said wild-type sequence, said downstream direction being the 5'→3' direction and said upstream direction being the 3'→5' direction; said cleavage thereby generating a four nucleotide 3' protruding sequence; said degenerate double-stranded target DNA sharing homology with said wild-type sequence in such a way that said homology still confers recognition and cleavage of said target DNA by said endonuclease with an efficiency of cleavage comprising between about 50 to 100% of the efficiency of cleavage of the corresponding wild-type sequence after a 1 to 16 hour reaction period, at an optimal temperature of 37° C.

3. An endonuclease according to claim 1, wherein N and N' are T and A, respectively.

4. An endonuclease according to claim 2, wherein the degeneracy of said target DNA is defined by base-pair substitutions effected at specific sites on said naturally occurring wild-type target sequence, said target DNA bearing said substitutions still being recognized and cleaved by said endonuclease, with an efficiency of cleavage being comprised between 50% and 100% of cleavage of said wild-type sequence, after a 1 to 16 hour reaction period, at an optimal temperature of 37° C.

5. An endonuclease according to claim 1 which recognizes and cleaves a double-stranded target DNA which nucleic acid sequence is selected from the group consisting of the following nucleic acid sequences:

| 5' | ACG | GTC | CTA | AGG | TAG | 3' | (SEQ ID NO:1) |
| 3' | TGC | CAG | GAT | TCC | ATC | 5' | |
| 5' | GCG | GTC | CTA | AGG | TAG | 3' | (SEQ ID NO:2) |
| 3' | CGC | CAG | GAT | TCC | ATC | 5' | |
| 5' | ACT | GTC | CTA | AGG | TAG | 3' | (SEQ ID NO:3) |
| 3' | TGA | CAG | GAT | TCC | ATC | 5' | |
| 5' | ACC | GTC | CTA | AGG | TAG | 3' | (SEQ ID NO:4) |
| 3' | TGG | CAG | GAT | TCC | ATC | 5' | |
| 5' | ACG | GTC | CAA | AGG | TAG | 3' | (SEQ ID NO:5) |
| 3' | TGC | CAG | GTT | TCC | ATC | 5' | |
| 5' | ACG | GTC | CTA | AGG | CAG | 3' | (SEQ ID NO:6) |
| 3' | TGC | CAG | GAT | TCC | GTC | 5' | |
| 5' | ACG | GTC | CTA | AGG | TCG | 3' | (SEQ ID NO:7) |
| 3' | TGC | CAG | GAT | TCC | AGC | 5' | |
| and | | | | | | | |
| 5' | ACG | GTC | CTA | AGG | TTG | 3' | (SEQ ID NO:8) |
| 3' | TGC | CAG | GAT | TCC | AAC | 5' | | wherein degeneracy of sequence is represented by underlined base-pair substitutions.

6. An endonuclease according to claim 4 which recognizes and cleaves a double-stranded target DNA which nucleic acid sequence is selected from the group consisting of the following nucleic acid sequences:

| 5' | ACG | GTC | CTA | AGG | TAG | 3' | (SEQ ID NO:1) |
| 3' | TGC | CAG | GAT | TCC | ATC | 5' | |
| 5' | GCG | GTC | CTA | AGG | TAG | 3' | (SEQ ID NO:2) |
| 3' | CGC | CAG | GAT | TCC | ATC | 5' | |
| 5' | ACT | GTC | CTA | AGG | TAG | 3' | (SEQ ID NO:3) |
| 3' | TGA | CAG | GAT | TCC | ATC | 5' | |
| 5' | ACC | GTC | CTA | AGG | TAG | 3' | (SEQ ID NO:4) |
| 3' | TGG | CAG | GAT | TCC | ATC | 5' | |
| 5' | ACG | GTC | CAA | AGG | TAG | 3' | (SEQ ID NO:5) |
| 3' | TGC | CAG | GTT | TCC | ATC | 5' | |
| 5' | ACG | GTC | CTA | AGG | CAG | 3' | (SEQ ID NO:6) |
| 3' | TGC | CAG | GAT | TCC | GTC | 5' | |
| 5' | ACG | GTC | CTA | AGG | TCG | 3' | (SEQ ID NO:7) |
| 3' | TGC | CAG | GAT | TCC | AGC | 5' | |
| and | | | | | | | |
| 5' | ACG | GTC | CTA | AGG | TTG | 3' | (SEQ ID NO:8) |
| 3' | TGC | CAG | GAT | TCC | AAC | 5' | | wherein base-pair substitutions are underlined.

7. An endonuclease according to claim 1 which recognizes and cleaves a double-stranded target DNA which nucleic acid sequence is selected from the group consisting of the following nucleic acid sequences:

| 5' | TA | ACG | GTC | CTA | AGG | TAG | 3' | (SEQ ID NO:9) |
| 3' | AT | TGC | CAG | GAT | TCC | ATC | 5' | |
| 5' | AA | ACG | GTC | CTA | AGG | TAG | 3' | (SEQ ID NO:10) |
| 3' | TT | TGC | CAG | GAT | TCC | ATC | 5' | |
| 5' | GA | ACG | GTC | CTA | AGG | TAG | 3' | (SEQ ID NO:11) |
| 3' | CT | TGC | CAG | GAT | TCC | ATC | 5' | |
| 5' | TT | ACG | GTC | CTA | AGG | TAG | 3' | (SEQ ID NO:12) |
| 3' | AA | TGC | CAG | GAT | TCC | ATC | 3' | |

-continued

| | | | | | | | |
|---|---|---|---|---|---|---|---|
| 5' TA | G̲CG | GTC | CTA | AGG | TAG | 3' | (SEQ ID NO:13) |
| 3' AT | C̲GC | CAG | GAT | TCC | ATC | 5' | |
| 5' TA | AC̲T | GTC | CTA | AGG | TAG | 3' | (SEQ ID NO.14) |
| 3' AT | TGA̲ | CAG | GAT | TCC | ATC | 5' | |
| 5' TA | ACC̲ | GTC | CTA | AGG | TAG | 3' | (SEQ ID NO:15) |
| 3' AT | TCG̲ | CAG | GAT | TCC | ATC | 5' | |
| 5' TA | ACG̲ | GTC | CA̲A | AGG | TAG | 3' | (SEQ ID NO:16) |
| 3' AT | TGC | CAG | GT̲T̲ | TCC | ATC | 5' | |
| 5' TA | ACG | GTC | CT̲A | AGG | C̲AG | 3' | (SEQ ID NO:17) |
| 3' AT | TGC | CAG | GAT | TCC | G̲TC | 5' | |
| 5' TA | ACG | GTC | CTA | AGG | T̲CG | 3' | (SEQ ID NO:18) |
| 3' AT | TGC | CAG | GAT | TCC | AG̲C | 5' | |
| and | | | | | | | |
| 5' TA | ACG | GTC | CTA | AGG | TT̲G | 3' | (SEQ ID NO:19) |
| 3' AT | TGC | CAG | GAT | TCC | AA̲C | 5' | | wherein degeneracy of sequence is represented by underlined base-pair substitutions.

8. An endonuclease according to claim 4 which recognizes and cleaves a double-stranded target DNA which nucleic acid sequence is selected from the group consisting of the following nucleic acid sequences:

| | | | | | | | |
|---|---|---|---|---|---|---|---|
| 5' TA | ACG | GTC | CTA | AGG | TAG | 3' | (SEQ ID NO:9) |
| 3' AT | TGC | CAG | GAT | TCC | ATC | 5' | |
| 5' A̲A̲ | ACG | GTC | CTA | AGG | TAG | 3' | (SEQ ID NO:10) |
| 3' T̲T̲ | TGC | CAG | GAT | TCC | ATC | 5' | |
| 5' G̲A | ACG | GTC | CTA | AGG | TAG | 3' | (SEQ ID NO:11) |
| 3' C̲T | TGC | CAG | GAT | TCC | ATC | 5' | |
| 5' T̲T̲ | ACG | GTC | CTA | AGG | TAG | 3' | (SEQ ID NO:12) |
| 3' A̲A̲ | TCG | CAG | GAT | TCC | ATC | 3' | |
| 5' TA | G̲CG | GTC | CTA | AGG | TAG | 3' | (SEQ ID NO:13) |
| 3' AT | C̲GC | CAG | GAT | TCC | ATC | 5' | |
| 5' TA | AC̲T | GTC | CTA | AGG | TAG | 3' | (SEQ ID NO:14) |
| 3' AT | TGA̲ | CAG | GAT | TCC | ATC | 5' | |
| 5' TA | ACC̲ | GTC | CTA | AGG | TAG | 3' | (SEQ ID NO:15) |
| 3' AT | TCG̲ | CAG | GAT | TCC | ATC | 5' | |
| 5' TA | ACG̲ | GTC | CA̲A | AGG | TAG | 3' | (SEQ ID NO:16) |
| 3' AT | TGC | CAG | GT̲T̲ | TCC | ATC | 5' | |
| 5' TA | ACG | GTC | CT̲A | AGG | C̲AG | 3' | (SEQ ID NO:17) |
| 3' AT | TGC | CAG | GAT | TCC | G̲TC | 5' | |
| 5' TA | ACG | GTC | CTA | AGG | T̲CG | 3' | (SEQ ID NO:18) |
| 3' AT | TGC | CAG | GAT | TCC | AG̲C | 5' | |
| and | | | | | | | |
| 5' TA | ACG | GTC | CTA | AGG | TT̲G | 3' | (SEQ ID NO:19) |
| 3' AT | TGC | CAG | GAT | TCC | AA̲C | 5' | | wherein base-pair substitutions are underlined.

9. An endonuclease according to claim 1 which recognizes and cleaves a double-stranded target DNA which nucleic acid sequence is selected from the group consisting of the following nucleic acid sequences:

| | | | | | | | | |
|---|---|---|---|---|---|---|---|---|
| 5' TA | ACG | GTC | CTA | AGG | TAG | CG | 3' | (SEQ ID NO:20) |
| 3' AT | TGC | CAG | GAT | TCC | ATC | CG | 5' | |
| 5' A̲A̲ | ACG | GTC | CTA | AGG | TAG | CG | 3' | (SEQ ID NO:21) |
| 3' T̲T̲ | TGC | CAG | GAT | TCC | ATC | GC | 5' | |
| 5' G̲A | ACG | GTC | CTA | AGG | TAG | CG | 3' | (SEQ ID NO:22) |
| 3' C̲T | TGC | CAG | CAT | TCC | ATC | CG | 5' | |
| 5' T̲T̲ | ACG | GTC | CTA | AGG | TAG | CG | 3' | (SEQ ID NO:23) |
| 3' A̲A̲ | TGC | CAG | GAT | TCC | ATC | CG | 5' | |
| 5' TA | G̲CG | GTC | CTA | AGG | TAG | CG | 3' | (SEQ ID NO:24) |
| 3' AT | C̲GC | CAG | CAT | TCC | ATC | GC | 5' | |
| 5' TA | AC̲T | GTC | CTA | AGG | TAG | CG | 3' | (SEQ ID NO:25) |
| 3' AT | TGA̲ | CAG | CAT | TCC | ATC | GC | 5' | |
| 5' TA | ACC̲ | GTC | CTA | AGG | TAG | CG | 3' | (SEQ ID NO:26) |
| 3' AT | TCG̲ | CAG | CAT | TCC | ATC | GC | 5' | |
| 5' TA | ACG̲ | GTC | CA̲A | AGG | TAG | CG | 3' | (SEQ ID NO:27) |
| 3' AT | TGC | CAG | GT̲T̲ | TCC | ATC | GC | 5' | |
| 5' TA | ACG | GTC | CT̲A | AGG | C̲AG | CG | 3' | (SEQ ID NO:28) |
| 3' AT | TGC | CAG | GAT | TCC | G̲TC | CG | 5' | |
| 5' TA | ACG | GTC | CTA | AGG | T̲CG | CG | 3' | (SEQ ID NO:29) |
| 3' AT | TGC | CAG | GAT | TCC | AG̲C | GC | 5' | |
| 5' TA | ACG | GTC | CTA | AGG | TT̲G | CG | 3' | (SEQ ID NO:30) |
| 3' AT | TGC | CAG | GAT | TCC | AA̲C | GC | 5' | |
| 5' TA | ACG | GTC | CTA | AGG | TAG | A̲G | 3' | (SEQ ID NO:31) |
| 3' AT | TGC | CAG | GAT | TCC | ATC | T̲C | 5' | |
| 5' TA | ACG | GTC | CTA | AGG | TAG | C̲T | 3' | (SEQ ID NO:32) |
| 3' AT | TGC | CAG | GAT | TCC | ATC | GA̲ | 5' | |
| and | | | | | | | | |
| 5' TA | ACG | GTC | CTA | AGG | TAG | CC̲ | 3' | (SEQ ID NO:33) |

```
3' AT  TGC  CAG  GAT  TCC  ATC  GG  5'
``` wherein degeneracy of sequence is represented by underlined base-pair substitutions.

10. An endonuclease according to claim 4 which recognizes and cleaves a double-stranded target DNA which nucleic acid sequence is selected from the consisting of the following nucleic acid sequences group:

```
5' TA  ACG  GTC  CTA  AGG  TAG  CG   3'  (SEQ ID NO:20)
3' AT  TGC  CAG  GAT  TCC  ATC  CG   5'
5' AA  ACG  GTC  CTA  AGG  TAG  CG   3'  (SEQ ID NO:21)
3' TT  TGC  CAG  GAT  TCC  ATC  GC   5'
5' GA  ACG  GTC  CTA  AGG  TAG  CG   3'  (SEQ ID NO:22)
3' CT  TGC  CAG  CAT  TCC  ATC  CG   5'
5' TT  ACG  GTC  CTA  AGG  TAG  CG   3'  (SEQ ID NO:23)
3' AA  TGC  CAG  GAT  TCC  ATC  CG   5'
5' TA  GCG  GTC  CTA  AGG  TAG  CG   3'  (SEQ ID NO:24)
3' AT  CGC  CAG  CAT  TCC  ATC  GC   5'
5' TA  ACT  GTC  CTA  AGG  TAG  CG   3'  (SEQ ID NO:25)
3' AT  TGA  CAG  CAT  TCC  ATC  GC   5'
5' TA  ACC  GTC  CTA  AGG  TAG  CG   3'  (SEQ ID NO:26)
3' AT  TCG  CAG  CAT  TCC  ATC  GC   5'
5' TA  ACG  GTC  CAA  AGG  TAG  CG   3'  (SEQ ID NO:27)
3' AT  TGC  CAG  GTT  TCC  ATC  GC   5'
5' TA  ACG  GTC  CTA  AGG  CAG  CG   3'  (SEQ ID NO:28)
3' AT  TGC  CAG  GAT  TCC  GTC  GC   5'
5' TA  ACG  GTC  CTA  AGG  TCG  CG   3'  (SEQ ID NO:29)
3' AT  TGC  CAG  GAT  TCC  AGC  GC   5'
5' TA  ACG  GTC  CTA  AGG  TTG  CG   3'  (SEQ ID NO:30)
3' AT  TGC  CAG  GAT  TCC  AAC  GC   5'
5' TA  ACG  GTC  CTA  AGG  TAG  AG   3'  (SEQ ID NO:31)
3' AT  TGC  CAG  GAT  TCC  ATC  TC   5'
5' TA  ACG  GTC  CTA  AGG  TAG  CT   3'  (SEQ ID NO:32)
3' AT  TGC  CAG  GAT  TCC  ATC  GA   5'
and
5' TA  ACG  GTC  CTA  AGG  TAG  CC   3'  (SEQ ID NO:33)
3' AT  TGC  CAG  GAT  TCC  ATC  GG   5'
``` wherein base-pair substitutions are underlined.

11. An endonuclease according to claim 2, wherein said wild-type sequence originates from the chloroplast of unicellular green alga *Chlamydomonas moewusii*.

* * * * *

UNITED STATES PATENT AND TRADEMARK OFFICE
CERTIFICATE OF CORRECTION

| | | |
|---|---|---|
| PATENT NO. : | 5,420,032 | PAGE 1 of 10 |
| DATED : | May 30, 1995 | |
| INVENTOR(S) : | Marshall et al. | |

It is certified that error appears in the above-identified patent and that said Letters Patent is hereby corrected as shown below:

```
In column 15, line 11, "SJC" should be --5JC--.
In column 15, line 11, "84" should be --B4--.
In column 1, line 45, "EcoRI" should be --Eco RI--.
In column 3, lines 3, 8 & 11, "EcoRI" should be --Eco RI--.
In column 7, line 30, "EcoRI" should be --Eco RI--.
In column 8, line 1, "EcoRI" should be --Eco RI--.
In column 9, lines 35 & 39, "EcoRI" should be --Eco RI--.
In column 11, lines 52 & 58, "EcoRI" should be --Eco RI--.
In column 6, line 36, " 3' "  (2nd occ.) should be --5'--.
In column 7, line 58, "euqametos" should be --eugametos--.
In column 9, line 20, "TaqI" should be --TagI--.
In column 9, line 25, "No. 34" should be --No:34--.
In column 9, line 28, "No. 35" should be --No:35--.
In column 11, line 47, "No. 36" should be --No:36--.
In column 11, line 49, "No. 37" should be --No:37--.
In column 12, line 11, "No. 38" should be --No:38--.
In column 12, line 14, "No. 39" should be --No:39--.
In column 9, lines 31 & 35, "Fig. 2" should be --Fig. 1--.
```

UNITED STATES PATENT AND TRADEMARK OFFICE
CERTIFICATE OF CORRECTION

PATENT NO. : 5,420,032

DATED : May 30, 1995

INVENTOR(S) : Marshall et al.

It is certified that error appears in the above-identified patent and that said Letters Patent is hereby corrected as shown below:

```
In column 11, line 4, "mR" should be --mM--.
In column 18, line 29, " 3' (2nd occ.) should be --5'--.
In column 18, line 14, "CAA" should be --CAA--.
In column 18, line 15, "GTT" should be --GTT--.
In column 48, claim 5, line 28, "TCG" should be --TCG--.
In column 48, claim 5, line 29, "AGC" should be --AGC--.
In column 52, claim 10, line 5, insert --group-- after the
word "the".
In column 52, claim 10, line 6, delete "group" after the
word "sequences".
In column 8, line 52, insert --(SEQ ID NO: 41)-- after the
numeral " 5' ".
In column 8, line 58, insert --(SEQ ID NO: 49)-- after the
numeral " 5' ".
In column 8, line 65, insert --(SEQ ID NO: 60)-- after the
numeral " 5' ".
In column 6, line 14, insert --(SEQ ID NO: 41)-- after the
number " 5' ".
```

UNITED STATES PATENT AND TRADEMARK OFFICE
CERTIFICATE OF CORRECTION

PATENT NO. : 5,420,032

DATED : May 30, 1995

INVENTOR(S) : Marshall et al.

It is certified that error appears in the above-identified patent and that said Letters Patent is hereby corrected as shown below:

```
In column 6, line 16, insert (SEQ ID NO: 42)-- after the
numeral " 5' ".
In column 6, line 18, insert (SEQ ID NO: 43)-- after the
numeral " 5' ".
In column 6, line 20, insert (SEQ ID NO: 44)-- after the
numeral " 5' ".
In column 6, line 22, insert (SEQ ID NO: 45)-- after the
numeral " 5' ".
In column 6, line 24, insert (SEQ ID NO: 46)-- after the
numeral " 5' ".
In column 6, line 26, insert (SEQ ID NO: 47)-- after the
numeral " 5' ".
In column 6, line 28, insert (SEQ ID NO: 48)-- after the
numeral " 5' ".
In column 6, line 30, insert (SEQ ID NO: 49)-- after the
numeral " 5' ".
In column 6, line 32, insert (SEQ ID NO: 50)-- after the
numeral " 5' ".
```

UNITED STATES PATENT AND TRADEMARK OFFICE
CERTIFICATE OF CORRECTION

PATENT NO. : 5,420,032      PAGE 4 of 10

DATED : May 30, 1995

INVENTOR(S) : Marshall et al.

It is certified that error appears in the above-identified patent and that said Letters Patent is hereby corrected as shown below:

```
In column 6, line 34, insert (SEQ ID NO: 51)-- after the
numeral " 5' ".
In column 6, line 36, insert (SEQ ID NO: 52)-- after the
numeral " 5' ".
In column 6, line 38, insert (SEQ ID NO: 53)-- after the
numeral " 5' ".
In column 6, line 40, insert (SEQ ID NO: 54)-- after the
numeral " 5' ".
In column 6, line 42, insert (SEQ ID NO: 55)-- after the
numeral " 5' ".
In column 6, line 44, insert (SEQ ID NO: 56)-- after the
numeral " 5' ".
In column 6, line 46, insert (SEQ ID NO: 57)-- after the
numeral " 5' ".
In column 6, line 48, insert (SEQ ID NO: 58)-- after the
numeral " 5' ".
In column 6, line 50, insert (SEQ ID NO: 59)-- after the
numeral " 5' ".
```

UNITED STATES PATENT AND TRADEMARK OFFICE
CERTIFICATE OF CORRECTION

PATENT NO. : 5,420,032

DATED : May 30, 1995

INVENTOR(S) : Marshall et al.

It is certified that error appears in the above-identified patent and that said Letters Patent is hereby corrected as shown below:

```
In column 6, line 52, insert (SEQ ID NO: 60)-- after the
numeral " 5' ".
In column 6, line 54, insert (SEQ ID NO: 61)-- after the
numeral " 5' ".
In column 6, line 56, insert (SEQ ID NO: 62)-- after the
numeral " 5' ".
In column 6, line 58, insert (SEQ ID NO: 63)-- after the
numeral " 5' ".
In column 6, line 60, insert (SEQ ID NO: 64)-- after the
numeral " 5' ".
In column 6, line 62, insert (SEQ ID NO: 65)-- after the
numeral " 5' ".
In column 6, line 64, insert (SEQ ID NO: 66)-- after the
numeral " 5' ".
In column 6, line 66, insert (SEQ ID NO: 67)-- after the
numeral " 5' ".
In column 6, line 68, insert (SEQ ID NO: 68)-- after the
numeral " 5' ".
```

UNITED STATES PATENT AND TRADEMARK OFFICE
CERTIFICATE OF CORRECTION

PATENT NO. :  5,420,032

DATED     :  May 30, 1995

INVENTOR(S) :  Marshall et al.

It is certified that error appears in the above-identified patent and that said Letters Patent is hereby corrected as shown below:

```
In column 6, line 70, insert (SEQ ID NO: 69)-- after the
numeral " 5' ".
In column 6, line 72, insert (SEQ ID NO: 70)-- after the
numeral " 5' ".
In column 6, line 74, insert (SEQ ID NO: 71)-- after the
numeral " 5' ".
In column 6, line 76, insert (SEQ ID NO: 72)-- after the
numeral " 5' ".
In column 7, line 2, insert (SEQ ID NO: 73)-- after the
numeral " 5' ".
In column 18, line 7, insert (SEQ ID NO: 41)-- after the
numeral " 5' ".
In column 18, line 9, insert (SEQ ID NO: 42)-- after the
numeral " 5' ".
In column 18, line 11, insert (SEQ ID NO: 43)-- after the
numeral " 5' ".
```

UNITED STATES PATENT AND TRADEMARK OFFICE
CERTIFICATE OF CORRECTION

PATENT NO. : 5,420,032

DATED : May 30, 1995

INVENTOR(S) : Marshall et al.

It is certified that error appears in the above-identified patent and that said Letters Patent is hereby corrected as shown below:

```
In column 18, line 13, insert (SEQ ID NO: 44)-- after the
numeral " 5' ".
In column 18, line 15, insert (SEQ ID NO: 45)-- after the
numeral " 5' ".
In column 18, line 17, insert (SEQ ID NO: 46)-- after the
numeral " 5' ".
In column 18, line 19, insert (SEQ ID NO: 47)-- after the
numeral " 5' ".
In column 18, line 21, insert (SEQ ID NO: 48)-- after the
numeral " 5' ".
In column 18, line 23, insert (SEQ ID NO: 49)-- after the
numeral " 5' ".
In column 18, line 25, insert (SEQ ID NO: 50)-- after the
numeral " 5' ".
In column 18, line 27, insert (SEQ ID NO: 51)-- after the
numeral " 5' ".
```

UNITED STATES PATENT AND TRADEMARK OFFICE
CERTIFICATE OF CORRECTION

PATENT NO. : 5,420,032          PAGE 8 of 10

DATED : May 30, 1995

INVENTOR(S) : Marshall et al.

It is certified that error appears in the above-identified patent and that said Letters Patent is hereby corrected as shown below:

```
In column 18, line 29, insert (SEQ ID NO: 52)-- after the
numeral " 5' ".
In column 18, line 31, insert (SEQ ID NO: 53)-- after the
numeral " 5' ".
In column 18, line 33, insert (SEQ ID NO: 54)-- after the
numeral " 5' ".
In column 18, line 35, insert (SEQ ID NO: 55)-- after the
numeral " 5' ".
In column 18, line 37, insert (SEQ ID NO: 56)-- after the
numeral " 5' ".
In column 18, line 39, insert (SEQ ID NO: 57)-- after the
numeral " 5' ".
In column 18, line 41, insert (SEQ ID NO: 58)-- after the
numeral " 5' ".
In column 18, line 43, insert (SEQ ID NO: 59)-- after the
numeral " 5' ".
```

UNITED STATES PATENT AND TRADEMARK OFFICE
CERTIFICATE OF CORRECTION

PATENT NO. : 5,420,032

DATED : May 30, 1995

INVENTOR(S) : Marshall et al.

It is certified that error appears in the above-identified patent and that said Letters Patent is hereby corrected as shown below:

```
In column 18, line 45, insert (SEQ ID NO: 60)-- after the
numeral " 5' ".
In column 18, line 47, insert (SEQ ID NO: 61)-- after the
numeral " 5' ".
In column 18, line 49, insert (SEQ ID NO: 62)-- after the
numeral " 5' ".
In column 18, line 51, insert (SEQ ID NO: 63)-- after the
numeral " 5' ".
In column 18, line 53, insert (SEQ ID NO: 64)-- after the
numeral " 5' ".
In column 18, line 55, insert (SEQ ID NO: 65)-- after the
numeral " 5' ".
In column 18, line 57, insert (SEQ ID NO: 66)-- after the
numeral " 5' ".
In column 18, line 59, insert (SEQ ID NO: 67)-- after the
numeral " 5' ".
In column 18, line 61, insert (SEQ ID NO: 68)-- after the
numeral " 5' ".
```

UNITED STATES PATENT AND TRADEMARK OFFICE
CERTIFICATE OF CORRECTION

PATENT NO. : 5,420,032

DATED : May 30, 1996

INVENTOR(S) : Marshall et al.

It is certified that error appears in the above-identified patent and that said Letters Patent is hereby corrected as shown below:

```
In column 18, line 63, insert (SEQ ID NO: 69)-- after the
numeral " 5' ".
In column 18, line 65, insert (SEQ ID NO: 70)-- after the
numeral " 5' ".
In column 18, line 67, insert (SEQ ID NO: 71)-- after the
numeral " 5' ".
In column 18, line 69, insert (SEQ ID NO: 72)-- after the
numeral " 5' ".
In column 18, line 71, insert (SEQ ID NO: 73)-- after the
numeral " 5' ".
```

Signed and Sealed this

Twenty-eighth Day of January, 1997

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 74

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ACGGTCCTAA GGTAG    15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCGGTCCTAA GGTAG    15

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ACTGTCCTAA GGTAG    15

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ACCGTCCTAA GGTAG    15

( 2 ) INFORMATION FOR SEQ ID NO:5:

( i ) SEQUENCE CHARACTERISTICS:
        ( A ) LENGTH: 15 base pairs

```
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ACGGTCCAAA GGTAG                                                                      15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ACGGTCCTAA GGCAG                                                                      15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ACGGTCCTAA GGTCG                                                                      15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ACGGTCCTAA GGTTG                                                                      15

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TAACGGTCCT AAGGTAG                                                                    17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:
```

AAACGGTCCT AAGGTAG 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GAACGGTCCT AAGGTAG 17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TTACGGTCCT AAGGTAG 17

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TAGCGGTCCT AAGGTAG 17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TAACTGTCCT AAGGTAG 17

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TAACGGTCCA AAGGTAG 17

( 2 ) INFORMATION FOR SEQ ID NO:16:

( i ) SEQUENCE CHARACTERISTICS:

-continued (A) LENGTH: 17 base pairs
            (B) TYPE: nucleic acid
            (C) STRANDEDNESS: single
            (D) TOPOLOGY: linear (i i) MOLECULE TYPE: DNA (genomic)

(x i) SEQUENCE DESCRIPTION: SEQ ID NO:16:

TAACGGTCCA AAGGTAG                                                              17

(2) INFORMATION FOR SEQ ID NO:17:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: DNA (genomic)

(x i) SEQUENCE DESCRIPTION: SEQ ID NO:17:

TAACGGTCCT AAGGTCG                                                              17

(2) INFORMATION FOR SEQ ID NO:18:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: DNA (genomic)

(x i) SEQUENCE DESCRIPTION: SEQ ID NO:18:

TAACGGTCCT AAGGTCG                                                              17

(2) INFORMATION FOR SEQ ID NO:19:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: DNA (genomic)

(x i) SEQUENCE DESCRIPTION: SEQ ID NO:19:

TAACGGTCCT AAGGTTG                                                              17

(2) INFORMATION FOR SEQ ID NO:20:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (i i) MOLECULE TYPE: DNA (genomic)

(x i) SEQUENCE DESCRIPTION: SEQ ID NO:20:

TAACGGTCCT AAGGTAGCG                                                            19

(2) INFORMATION FOR SEQ ID NO:21:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (i i) MOLECULE TYPE: DNA (genomic)

( x i ) SEQUENCE DESCRIPTION: SEQ ID NO:21:

AAACGGTCCT AAGGTAGCG                                                                    19

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GAACGGTCCT AAGGTAGCG                                                                    19

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

TTACGGTCCT AAGGTAGCG                                                                    19

( 2 ) INFORMATION FOR SEQ ID NO:24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

TAGCGGTCCT AAGGTAGCG                                                                    19

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

TAACTGTCCT AAGGTAGCG                                                                    19

( 2 ) INFORMATION FOR SEQ ID NO:26:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TAACGGTCCT AAGGCAGCG                                                                    19

( 2 ) INFORMATION FOR SEQ ID NO:27:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:27:

TAACGGTCCA AAGGTAGCG      19

( 2 ) INFORMATION FOR SEQ ID NO:28:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

TAACGGTCCT AAGGCAGCGA TTGCCAGGAT TCCGTCGC      38

( 2 ) INFORMATION FOR SEQ ID NO:29:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TAACGGTCCT AAGGTCGCG      19

( 2 ) INFORMATION FOR SEQ ID NO:30:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

TAACGGTCCT AAGGTTGCG      19

( 2 ) INFORMATION FOR SEQ ID NO:31:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TAACGGTCCT AAGGTAGAG      19

( 2 ) INFORMATION FOR SEQ ID NO:32:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

TAACGGTCCT AAGGTAGCT                                                                          19

( 2 ) INFORMATION FOR SEQ ID NO:33:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TAACGGTCCT AAGGTAGCC                                                                          19

( 2 ) INFORMATION FOR SEQ ID NO:34:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

CATGTCCAAC TTCATCCTGA AAC                                                                     23

( 2 ) INFORMATION FOR SEQ ID NO:35:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

CGGTTTCAGG ATGAAGTTGG A                                                                       21

( 2 ) INFORMATION FOR SEQ ID NO:36:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

GATCCTAACT ATAACGGTCC TAAGGTAGCG AG                                                           32

( 2 ) INFORMATION FOR SEQ ID NO:37:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GATCCTCGCT ACCTTAGGAC CGTTATAGTT AG                                                           32

( 2 ) INFORMATION FOR SEQ ID NO:38:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:38:

ACAGGTCTCC GCAAAGTCGT A 21

( 2 ) INFORMATION FOR SEQ ID NO:39:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:39:

AATACGACTC ACTATAG 17

( 2 ) INFORMATION FOR SEQ ID NO:40:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:40:

TAACTATAAC GGTCCTAAGG TAGCGA 26

( 2 ) INFORMATION FOR SEQ ID NO:41:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:41:

CTACCTTAGG ACCGT 15

( 2 ) INFORMATION FOR SEQ ID NO:42:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

CTACCTTAGG ACCGC 15

( 2 ) INFORMATION FOR SEQ ID NO:43:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:43:

CTACCTTAGG ACAGT 15

( 2 ) INFORMATION FOR SEQ ID NO:44:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

CTACCTTAGG ACGGT 15

( 2 ) INFORMATION FOR SEQ ID NO:45:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

CTACCTTTGG ACCGT 15

( 2 ) INFORMATION FOR SEQ ID NO:46:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CTGCCTTAGG ACCGT 15

( 2 ) INFORMATION FOR SEQ ID NO:47:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

CGACCTTAGG ACCGT 15

( 2 ) INFORMATION FOR SEQ ID NO:48:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

CAACCTTAGG ACCGT 15

( 2 ) INFORMATION FOR SEQ ID NO:49:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

CTACCTTAGG ACCGTTA      17

( 2 ) INFORMATION FOR SEQ ID NO:50:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

CTACCTTAGG ACCGTTT      17

( 2 ) INFORMATION FOR SEQ ID NO:51:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

CTACCTTAGG ACCGTTC      17

( 2 ) INFORMATION FOR SEQ ID NO:52:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

CTACCTTAGG ACCGTAA      17

( 2 ) INFORMATION FOR SEQ ID NO:53:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

CTACCTTAGG ACCGCTA      17

( 2 ) INFORMATION FOR SEQ ID NO:54:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:54:

CTACCTTAGG ACAGTTA 17

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:55:

CTACCTTAGG ACGCTTA 17

(2) INFORMATION FOR SEQ ID NO:56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:56:

CTACCTTTGG ACCGTTA 17

(2) INFORMATION FOR SEQ ID NO:57:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:57:

CTGCCTTAGG ACCGTTA 17

(2) INFORMATION FOR SEQ ID NO:58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:58:

CGACCTTAGG ACCGTTA 17

(2) INFORMATION FOR SEQ ID NO:59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:59:

CAACCTTAGG ACCGTTA 17

( 2 ) INFORMATION FOR SEQ ID NO:60:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

GCCTACCTTA GGACCGTTA                                      19

( 2 ) INFORMATION FOR SEQ ID NO:61:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

CGCTACCTTA GGACCGTTT                                      19

( 2 ) INFORMATION FOR SEQ ID NO:62:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

GCCTACCTTA CGACCGTTC                                      19

( 2 ) INFORMATION FOR SEQ ID NO:63:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

GCCTACCTTA GGACCGTAA                                      19

( 2 ) INFORMATION FOR SEQ ID NO:64:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

CGCTACCTTA CGACCGCTA                                      19

( 2 ) INFORMATION FOR SEQ ID NO:65:

( i ) SEQUENCE CHARACTERISTICS:
        ( A ) LENGTH: 19 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:65:

CGCTACCTTA CGACAGTTA                                                           19

( 2 ) INFORMATION FOR SEQ ID NO:66:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

CGCTACCTTA CGACGCTTA                                                           19

( 2 ) INFORMATION FOR SEQ ID NO:67:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

CGCTACCTTT GGACCGTTA                                                           19

( 2 ) INFORMATION FOR SEQ ID NO:68:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

CGCTGCCTTA GGACCGTTA                                                           19

( 2 ) INFORMATION FOR SEQ ID NO:69:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

CGCGACCTTA GGACCGTTA                                                           19

( 2 ) INFORMATION FOR SEQ ID NO:70:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

CGCAACCTTA GGACCGTTA                                                           19

( 2 ) INFORMATION FOR SEQ ID NO:71:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:71:

CTCTACCTTA GGACCGTTA                    19

( 2 ) INFORMATION FOR SEQ ID NO:72:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

AGCTACCTTA GGACCGTTA                    19

( 2 ) INFORMATION FOR SEQ ID NO:73:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:73:

GGCTACCTTA GGACCGTTA                    19

( 2 ) INFORMATION FOR SEQ ID NO:74:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

TCGCTACCTT AGGACCGTTA TAGTTA            26